US007225014B1

United States Patent
Province

(10) Patent No.: US 7,225,014 B1
(45) Date of Patent: May 29, 2007

(54) ANTI-ARRHYTHMIA THERAPY BASED ON SPATIAL AND/OR TEMPORAL INFORMATION

(75) Inventor: Rose A. Province, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 321 days.

(21) Appl. No.: 10/848,853

(22) Filed: May 18, 2004

(51) Int. Cl.
*A61B 5/0402* (2006.01)
*A61N 1/36* (2006.01)

(52) U.S. Cl. .............................. 600/516; 607/9; 607/25
(58) Field of Classification Search ............... 600/513, 600/515–518, 508; 607/4–5, 9, 1, 14
See application file for complete search history.

(56) References Cited

U.S. PATENT DOCUMENTS

| | | | | |
|---|---|---|---|---|
| 6,134,470 | A * | 10/2000 | Hartlaub | 607/14 |
| 6,381,493 | B1 | 4/2002 | Stadler et al. | 607/9 |
| 6,690,971 | B2 * | 2/2004 | Schauerte et al. | 607/17 |
| 7,072,711 | B2 * | 7/2006 | Girouard et al. | 607/3 |
| 2002/0138106 | A1 | 9/2002 | Christini et al. | 607/9 |
| 2003/0060724 | A1 * | 3/2003 | Thiagarajan et al. | 600/515 |
| 2005/0049516 | A1 * | 3/2005 | Ideker | 600/516 |

FOREIGN PATENT DOCUMENTS

WO WO 02/34123 A2 5/2002

OTHER PUBLICATIONS

Watanabe, et al., "Mechanisms for Discordant Alternans", Journal of Cardiovascular Electrophysiology, vol. 12, No. 2, Feb. 2001, pp. 196-206.
Can, et al., "Physiological Mechanisms Influencing Cardiac Repolarization and QT Intervals", Cardiac Electrophysiology Review 2002, vol. 6, No. 3, pp. 278-281.
Nearing, et al., "Progressive Increases in Complexity of T-Wave Oscillations Herald Ischemia-Induced Ventricular Fibrillation", Circulation Research, Oct. 18, 2002, vol. 91, No. 8, pp. 727-732.

(Continued)

*Primary Examiner*—Carl Layno
*Assistant Examiner*—Jessica L. Reidel
(74) *Attorney, Agent, or Firm*—Steven M. Mitchell

(57) ABSTRACT

Receiving an action potential signal associated with a myocardial contraction sensed at a myocardial site, receiving an action potential signal associated with the myocardial contraction sensed at a different myocardial site, comparing a common characteristics of each of the action potential signals wherein the common characteristics relates to at least one member selected from the group consisting of depolarization of tissue at the myocardial sites and repolarization of tissue at the myocardial sites, and, based on the comparing, deciding whether to call for anti-arrhythmia therapy.

26 Claims, 19 Drawing Sheets

OTHER PUBLICATIONS

Banville, et al., "Effect of Action Potential Duration and Conduction Velocity Restitution and Their Spatial Dispersion on Alternans and the Stability of Arrhythmias", Journal of Cardiovascular Electrophysiology, vol.13, No. 11, Nov. 2002, pp. 1141-1149.

Konta, et al., "Significance of Discordant ST Alternans in Ventricular Fibrillation", Circulation, vol. 82, No. 6, Dec. 1990, pp. 2185-2189.

Rubenstein, et al., "Premature Beats Elicit a Phase Reversal of Mechanoelectrical Alternans in Cat Ventricular Myocytes", Circulation, vol. 91, No. 1, Jan. 1, 1995, pp. 201-214.

Pastore, et al., "Mechanism Linking T-Wave Alternans to the Genesis of Cardiac Fibrillation", Circulation, vol. 99, Mar. 16, 1999, pp. 1385-1394.

Pastore, et al., "Role of Structural Barriers in the Mechanism of Alternans-Induced Reentry", Circulation, vol. 87, Dec. 8-22, 2000, pp. 1157-1163.

Qu, et al., "Mechanisms of Discordant Alternans and Induction of Reentry in Simulated Cardiac Tissue", Circulation, vol. 102, Oct. 3, 2002, pp. 1664-1670.

Hashimoto, et al., "Effects of the Ventricular Premature Beat on the Alternation of the Repolarization Phase in Ischemic Myocardium during Acute Coronary Occlusion in Dogs", J. Electrocardiology 17, (3), 1984, pp. 229-238.

Hashimoto, et al., "Potentiating Effects of a Ventricular Premature Beat on the Alternation of the ST-T Complex of Epicardial Electrograms and the Incidence of Ventricular Arrhythmias during Acute Coronary Occlusions in Dogs", J. Electrocardiology 17, (3), 1984, pp. 289-302.

Hashimoto, et al., "Evidence for a link between mechanical and electrical alternans in acutely ischaemic myocardium of anesthetized dogs", Acta Physiol Scand 1991, 141, pp. 63-70.

Murphy, et al., "Regional electromechanical alternans in anesthetized pig hearts: modulation b mechanoelectric feedback", the American Physiological Society, Nov. 1995 (5 Pt2), pp. H1726-H1735.

Tachibana, et al., "Discordant S-T alternans contributes to formation of reentry: a possible mechanism of reperfusion arrhythmia", AJP—Heart and Circulatory Physiology, vol. 275, Issue 1, Jul. 1998, pp. H116-H121.

* cited by examiner

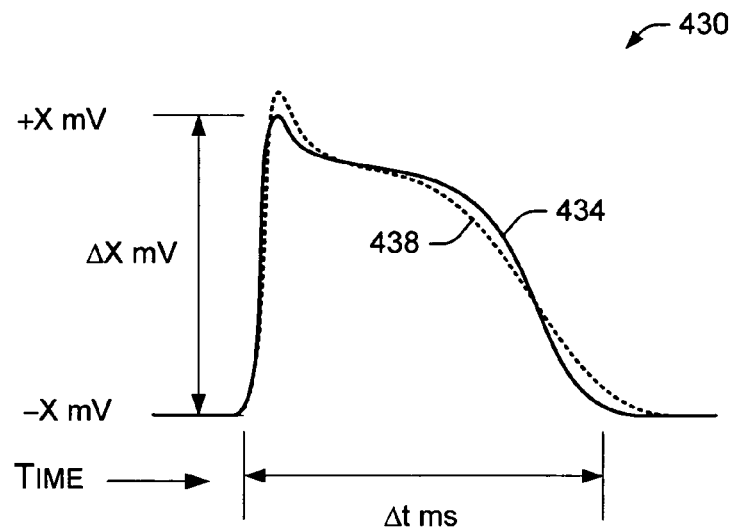
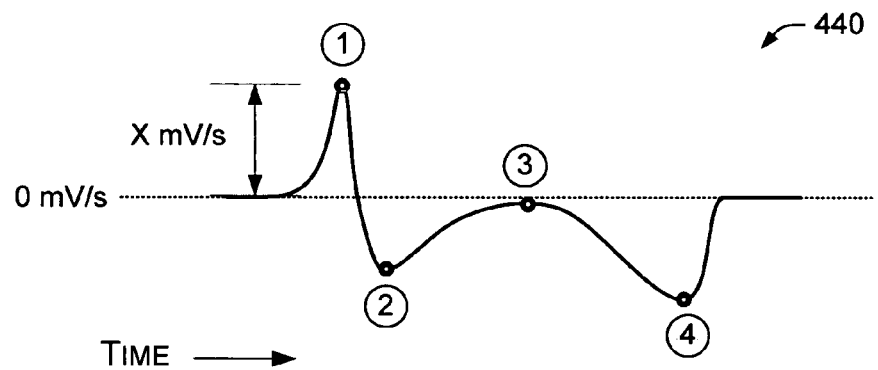
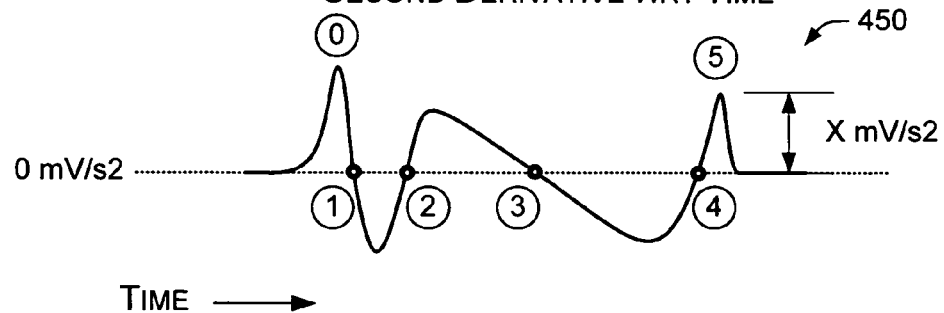
Fig.5

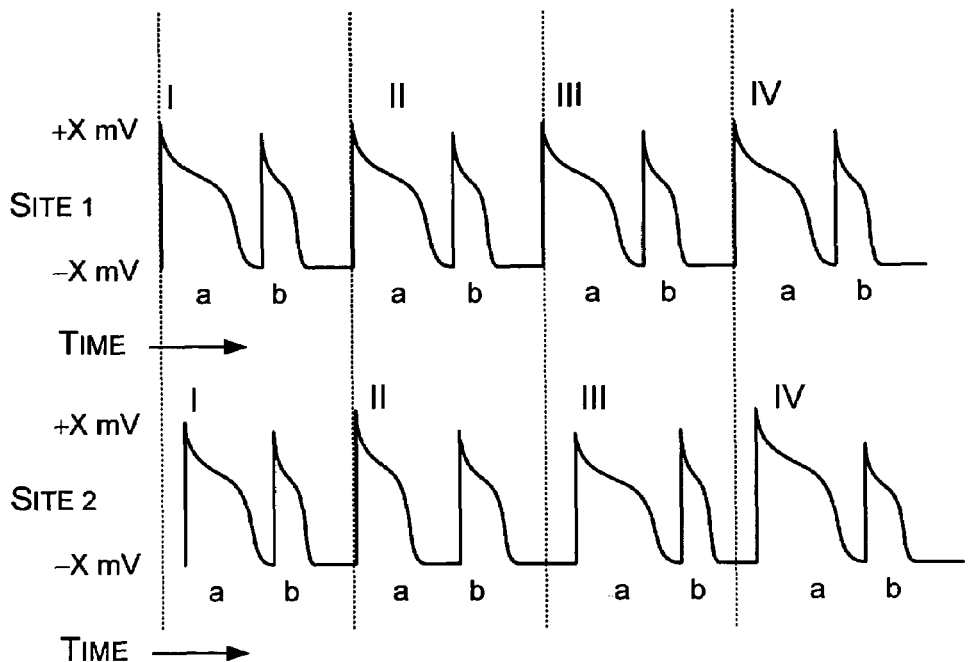

EXEMPLARY ACTION POTENTIAL ALTERNANS
800

TEMPORALLY AND SPATIALLY DISCORDANT FOR COMPARISON OF SITE I AND SITE II

CHARACTERISTICS

|  | I | II | III | IV |
|---|---|---|---|---|
| SITE 1 | | | | |
| AMPLITUDE | $A(I,1)$ | $A(II,1)$ | $A(III,1)$ | $A(IV,1)$ |
| DURATION | $\Delta T(I,1)$ | $\Delta T(II,1)$ | $\Delta T(III,1)$ | $\Delta T(IV,1)$ |
| T WAVE START | $TS(I,1)$ | $TS(II,1)$ | $TS(III,1)$ | $TS(IV,1)$ |
| SITE 2 | | | | |
| AMPLITUDE | $A(I,2)$ | $A(II,2)$ | $A(III,2)$ | $A(IV,2)$ |
| DURATION | $\Delta T(I,2)$ | $\Delta T(II,2)$ | $\Delta T(III,2)$ | $\Delta T(IV,2)$ |
| T WAVE START | $TS(I,2)$ | $TS(II,2)$ | $TS(III,2)$ | $TS(IV,2)$ |

Fig.8

EXEMPLARY AP ALTERNANS
CHARACTERISTICS
1000

| SITE 1 | I | II | III | IV |
|---|---|---|---|---|
| AMPLITUDE | A(Ia,1) | A(IIa,1) | A(IIIa,1) | A(IVa,1) |
| DURATION | Δt(Ia,1) | Δt(IIa,1) | Δt(IIIa,1) | Δt(IVa,1) |
| T WAVE START | TS(Ia,1) | TS(IIa,1) | TS(IIIa,1) | TS(IVa,1) |
| AMPLITUDE | A(Ib,1) | A(IIb,1) | A(IIIb,1) | A(IVb,1) |
| DURATION | Δt(Ib,1) | Δt(IIb,1) | Δt(IIIb,1) | Δt(IVb,1) |
| T WAVE START | TS(Ib,1) | TS(IIb,1) | TS(IIIb,1) | TS(IVb,1) |
| ALTERNANS | ΔA(I,1) | ΔA(II,1) | ΔA(III,1) | ΔA(IV,1) |
| ANALYSIS | ΔΔt(I,1) | ΔΔt(II,1) | ΔΔt(III,1) | ΔΔt(IV,1) |
| SITE 1 | ΔTS(I,1) | ΔTS(II,1) | ΔTS(III,1) | ΔTS(IV,1) |

| SITE 2 | I | II | III | IV |
|---|---|---|---|---|
| AMPLITUDE | A(Ia,2) | A(IIa,2) | A(IIIa,2) | A(IVa,2) |
| DURATION | Δt(Ia,2) | Δt(IIa,2) | Δt(IIIa,2) | Δt(IVa,2) |
| T WAVE START | TS(Ia,2) | TS(IIa,2) | TS(IIIa,2) | TS(IVa,2) |
| AMPLITUDE | A(Ib,2) | A(IIb,2) | A(IIIb,2) | A(IVb,2) |
| DURATION | Δt(Ib,2) | Δt(IIb,2) | Δt(IIIb,2) | Δt(IVb,2) |
| T WAVE START | TS(Ib,2) | TS(IIb,2) | TS(IIIb,2) | TS(IVb,2) |
| ALTERNANS | ΔA(I,2) | ΔA(II,2) | ΔA(III,2) | ΔA(IV,2) |
| ANALYSIS | ΔΔt(I,2) | ΔΔt(II,2) | ΔΔt(III,2) | ΔΔt(IV,2) |
| SITE 2 | ΔTS(I,2) | ΔTS(II,2) | ΔTS(III,2) | ΔTS(IV,2) |

Fig.10

EXEMPLARY AP ALTERNANS
SPATIAL CHARACTERISTICS
1100

Single AP at each Site (e.g., 1, 2, ... n)

Adiff = A(Ia,1) - A(Ia, 2)

$\Delta$tdiff = $\Delta$t(Ia,1) - $\Delta$t(Ia,2)

time activation-diff = tactivation(Ia,1) - tactivation(Ia,2)

time repolarization-diff = trepolarization(Ia,1) - trepolarization(Ia,2)

TSdiff = TS(Ia,1) - TS(Ia,2)

Single AP at each Site (e.g., 1, 2, ... n)

Adiff = A(Ib,1) - A(Ib, 2)

$\Delta$tdiff = $\Delta$t(Ib,1) - $\Delta$t(Ib,2)

time activation-diff = tactivation(Ib,1) - tactivation(Ib,2)

time repolarization-diff = trepolarization(Ib,1) - trepolarization(Ib,2)

TSdiff = TS(Ib,1) - TS(Ib,2)

Alternans Pair AP at each Site (e.g., 1, 2, ... n)

$\Delta$Adiff = $\Delta$A(I,1) - $\Delta$A(I, 2)

$\Delta\Delta$tdiff = $\Delta\Delta$t(I,1) - $\Delta\Delta$t(I,2)

$\Delta$time activation-diff = $\Delta$tactivation(I,1) - $\Delta$tactivation(I,2)

$\Delta$time repolarization-diff = $\Delta$trepolarization(I,1) - $\Delta$trepolarization(I,2)

$\Delta$TSdiff = $\Delta$TS(I,1) - $\Delta$TS(I,2)

Fig.11

SINGLE AP AT EACH SITE (E.G., THREE SITES)
1200

AP Amplitude
   Adiff = [A(Ia,1) - A(Ia, 2)] + [A(Ia,1) - A(Ia, 3)] + [A(Ia,2) - A(Ia, 3)].

A-ABSdiff =   ABS[A(Ia,1) - A(Ia, 2)] +
                 ABS[A(Ia,1) - A(Ia, 3)] +
                 ABS[A(Ia,2) - A(Ia, 3)].

AP Duration
   $\Delta$tdiff = [$\Delta$t(Ia,1) - $\Delta$t(Ia,2)] + [$\Delta$t(Ia,1) - $\Delta$t(Ia,3)] + [$\Delta$t(Ia,2) - $\Delta$t(Ia,3)].

$\Delta$t-ABSdiff =   ABS[$\Delta$t(Ia,1) - $\Delta$t(Ia,2)] +
                  ABS[$\Delta$t(Ia,1) - $\Delta$t(Ia,3)] +
                  ABS[$\Delta$t(Ia,2) - $\Delta$t(Ia,3)].

AP Activation Time or Repolarization End Time
   time activation-diff =   [tactivation(Ia,1) - tactivation(Ia,2)] +
                            [tactivation(Ia,1) - tactivation(Ia,3)] +
                            [tactivation(Ia,2) - tactivation(Ia,3)].

time activation-ABSdiff =   ABS[tactivation(Ia,1) - tactivation(Ia,2)] +
                               ABS[tactivation(Ia,1) - tactivation(Ia,3)] +
                               ABS[tactivation(Ia,2) - tactivation(Ia,3)].

time repolarization-diff =   [trepolarization(Ib,1) - trepolarization(Ia,2)] +
                                [trepolarization(Ib,1) - trepolarization(Ia,3)] +
                                [trepolarization(Ib,2) - trepolarization(Ia,3)].

time repolarization-ABSdiff =   ABS[trepolarization(Ib,1) - trepolarization(Ia,2)] +
                                   ABS[trepolarization(Ib,1) - trepolarization(Ia,3)] +
                                   ABS[trepolarization(Ib,2) - trepolarization(Ia,3)].

AP Start of T wave
   TSdiff = [TS(Ia,1) - TS(Ia,2)] + [TS(Ia,1) - TS(Ia,3)] + [TS(Ia,2) - TS(Ia,3)].

TS-ABSdiff =   ABS[TS(Ia,1) - TS(Ia,2)] +
                  ABS[TS(Ia,1) - TS(Ia,3)] +
                  ABS[TS(Ia,2) - TS(Ia,3)].

Fig.12

COMPARING WITH RESPECT TO BASELINE
1300

AP Amplitude
    ΔAdiff = Adiff-baseline − Adiff

ΔA-ABSdiff = A-ABSdiff-baseline − A-ABSdiff

AP Duration
    ΔΔtdiff = Δtdiff-baseline − Δtdiff

ΔΔt-ABSdiff = Δt-ABSdiff-baseline − Δt-ABSdiff

AP Activation TIme or Repolarization End Time
    Δtime activation-diff = time activation-diff-baseline − time activation-diff Δtime activation-ABSdiff = time activation-ABSdiff-baseline − time activation-ABSdiff Δtime repolarization-diff = time repolarization-diff-baseline − time repolarization-diff Δtime repolarization-ABSdiff = time repolarization-ABSdiff-baseline − time repolarization-ABSdiff AP Start of T wave
    ΔTSdiff = TSdiff-baseline − TSdiff ΔTS-ABSdiff = TS-ABSdiff-baseline − TS-ABSdiff

Fig.13

ANTI-ARRHYTHMIA THERAPY BASED ON SPATIAL AND/OR TEMPORAL INFORMATION

TECHNICAL FIELD

Subject matter presented herein relates generally to cardiac pacing and/or stimulation therapy. Various examples concern anti-arrhythmia therapy based on spatial and/or temporal information.

BACKGROUND

Repolarization occurs after myocardial contraction. Electrocardiograms (ECGs) collected from electrodes placed on the surface of a patient's body can exhibit cardiac repolarization and, in particular, repolarization due to contraction of ventricular myocardium. Repolarization associated with normal ventricular contraction is typically referred to as a "T wave". An ECG T wave is representative of a sum of repolarizations of many individual myocardial cells; hence, an ECG T wave exhibits little spatial information. However, where spatial repolarization heterogeneity exists among the many cells, an ECG T wave may exhibit some differences when compared to an ECG T wave from a more homogenous repolarization. In general, exhibited differences in ECG T wave morphology are referred to commonly as T wave alternans (i.e., alternating T wave morphology).

Various studies have linked the presence of T wave alternans to risk of ventricular arrhythmia, a major cause of sudden cardiac death. The link suggests that an increase in heterogeneity of ventricular myocardial repolarization indicates an increased risk of ventricular arrhythmia and possibly even an imminent onset of ventricular arrhythmia. Hence, information contained in an ECG T wave may possibly be used to prevent cardiac death.

Some studies have proposed implantable cardiac pacemakers that use T wave alternans detection. In general, such devices rely on intraelectrocardiograms (IEGMs) rather than surface ECGs to detect T wave alternans. Information exhibited by IEGMs differs from that of surface ECGs because in IEGMs, measurement electrodes are physically and/or electrically more intimately in contact with myocardial tissue. IEGMs typically include information same or similar to waveforms characteristic of cellular action potentials such as monophasic action potentials (MAPs), etc.

While the nature of information in ECGs and IEGMs differs, such devices typically seek to collect and analyze IEGM information to discern T wave alternans in a manner akin to that used for surface ECGs. For example, one study used a unipolar electrode configuration with an electrode in the right ventricular apex because repolarization alternans results from a spatially extended dispersion of ventricular repolarization and because the unipolar voltage vector covers a greater area of ventricular myocardium than standard bipolar recordings. Again, surface ECGs also measure a spatially extended dispersion of ventricular repolarization and have a voltage vector that covers a large area of the ventricular myocardium.

While such spatially extended measurements of ventricular repolarization may prove helpful in assessing risk or imminent onset of arrhythmia, a need exists for techniques that can measure and use local and/or spatial information. Various exemplary methods and/or devices described herein include use of local and/or spatial information.

SUMMARY

An exemplary method includes receiving an action potential signal associated with a myocardial contraction sensed at a myocardial site, receiving an action potential signal associated with the myocardial contraction sensed at a different myocardial site, comparing a common characteristic of each of the action potential signals wherein the common characteristic relates to at least one member selected from the group consisting of depolarization of tissue at the myocardial sites and repolarization of tissue at the myocardial sites, and, based on the comparing, deciding whether to call for anti-arrhythmia therapy. Anti-arrhythmia therapy may include pacing, stimulation (cardiac and/or nerve), drug, ablation and/or other therapies. Other exemplary methods, device, systems, etc., are also disclosed.

BRIEF DESCRIPTION OF THE DRAWINGS

Features and advantages of the described implementations can be more readily understood by reference to the following description taken in conjunction with the accompanying drawings.

FIG. 5 is a diagram of a monophasic action potential and a first and a second derivative of the monophasic action potential with respect to time.

FIG. 8 is a diagram of exemplary alternans and characteristics thereof.

FIG. 10 is a listing of various characteristics for waveforms at a plurality of sensing sites.

FIG. 11 is a listing of spatial characteristics for waveforms at a plurality of sensing sites.

FIG. 12 is a listing of exemplary analyses for waveform characteristics at a plurality of sensing sites.

FIG. 13 is a listing of exemplary analyses for waveform characteristics versus baseline (e.g., standard) characteristics.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like are typically numerals or reference designators will be used to reference like parts or elements throughout.

Exemplary Stimulation Device

The techniques described below are intended to be implemented in connection with any stimulation device that is configured or configurable to delivery cardiac therapy and/or sense information germane to cardiac therapy.

Figure 1:
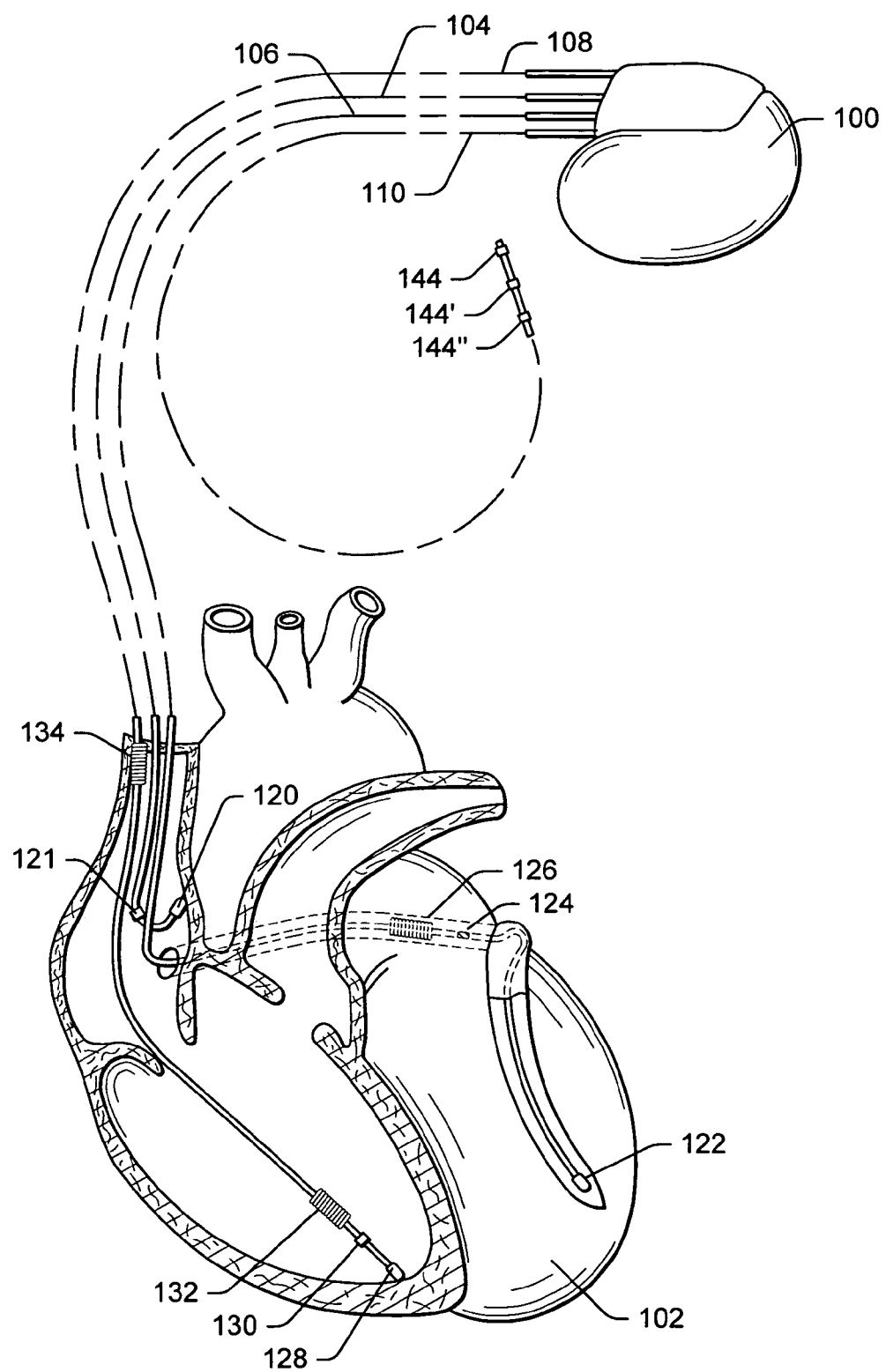
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which are incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
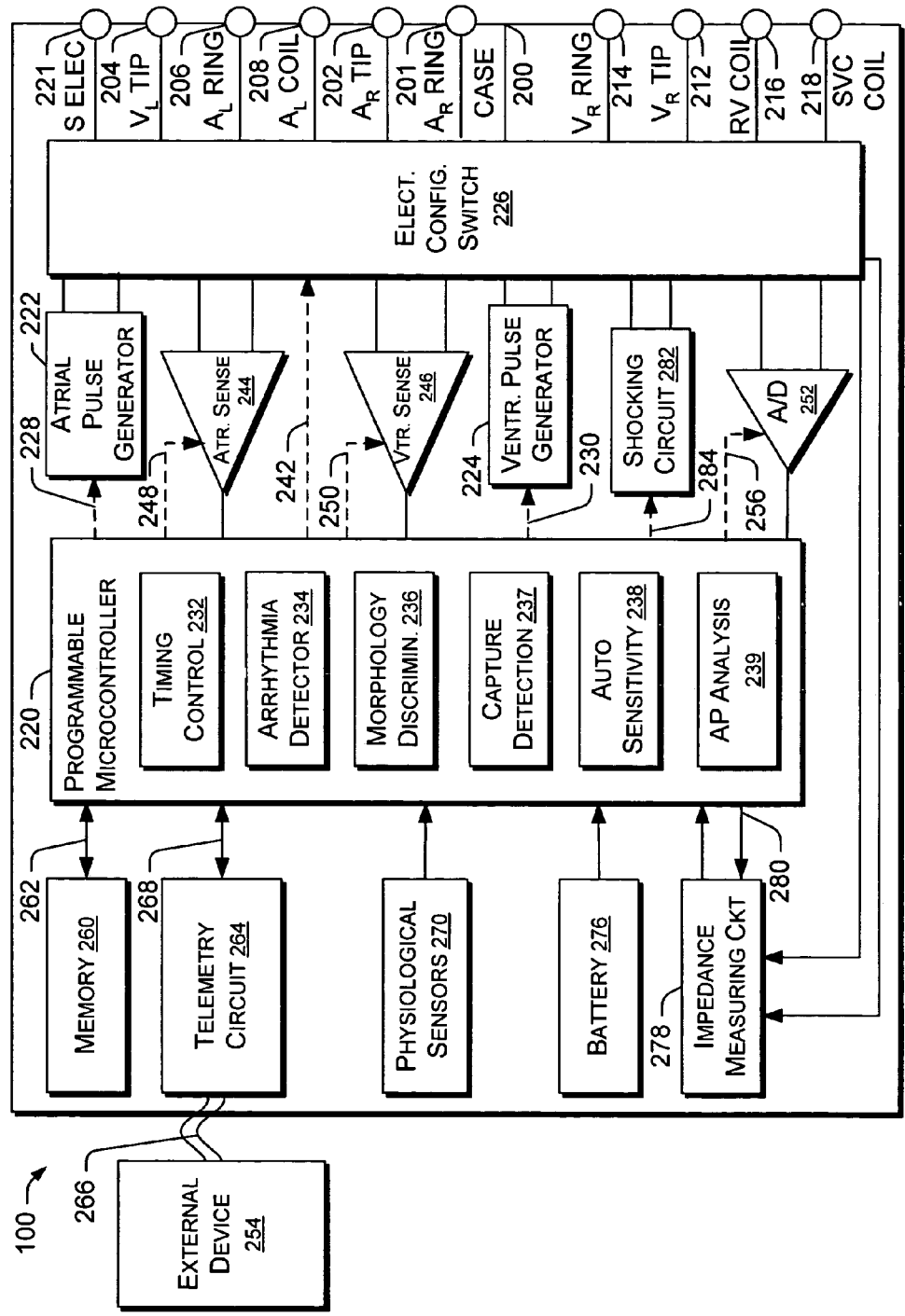
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A—A) delay, or interventricular conduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237, an auto sensing module 238 and an action potential (AP)-module 239. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The action potential module 239, as described herein, may aid in acquisition, analysis, etc., of action potentials. Action potentials may include monophasic action potentials, intracardiacelectrograms (IEGMs), etc., and various features thereof such as, but not limited to, polarization and repolarization.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. Such a module is optionally suitable for performing various exemplary methods described herein. For example, such a module (e.g., the module 234, the module 239, etc.) optionally allows for analyses related to action potentials (e.g., MAPs, T waves, etc.) and characteristics thereof (e.g., alternans, activation times, repolarization times, derivatives, etc.).

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Ventricular Arrhythmias

As mentioned, ventricular arrhythmia is a leading cause of sudden cardiac death. Detection of ventricular arrhythmia and/or precursors thereto can help in prevention of such deaths. The aforementioned exemplary implantable cardiac device 100 includes an ability to detect arrhythmia and/or precursors thereto and to respond to such detection. One particular response includes delivery of one or more stimuli to the heart. The exemplary implantable 100 may additionally or alternatively provide a response that includes autonomic nerve stimulation.

Ventricular arrhythmias often involve reentry wavefronts or circuits that travel around poorly conducting or unresponsive cardiac scar tissue or that travel in a wholly functional myocardial region. As described herein, spatial information may help determine locations of such reentry circuits (e.g., their spatio-temporal characteristics). Some studies of pacing to terminate ventricular arrhythmias suggest pacing or delivering stimulation at a site wherein the position of the site is based on location of a reentry circuit. Various studies suggest pacing or delivering at a site proximate to the reentry circuit while others suggest pacing or delivering at a site removed from the reentry circuit. Of course, sometimes pacing or delivering is limited to a single site; consider, for example, an implantable cardiac device having a single lead with a pacing electrode positioned in a patient's right ventricle. In such instances, spatial and/or temporal information pertaining to a reentry circuit may prove beneficial, for example, in determining a pacing time and/or pacing amplitude, frequency, etc. As described herein, such information optionally includes information regarding homogeneity or heterogeneity of a reentry circuit. Further, characteristics of a reentry circuit optionally include information regarding ischemia, conduction velocity, etc.

Various factors may affect successful termination of a ventricular arrhythmia. Such factors include, but are not limited to, arrhythmia rate (e.g., path length and conduction velocity), refractory period at a pacing or stimulation site and/or in a reentry circuit, conduction path from pacing or stimulation site to a reentry circuit (e.g., including conduction velocity, conduction time, etc.), reentry circuit gap characteristics. See, e.g., Sinha, et al., "Critical role of inhomogeneities in pacing termination of cardiac reentry", *CHAOS,* 12(3): 893–902 (2002).

While various exemplary mechanisms presented herein optionally include stimulation or pacing based arrhythmia termination and/or prevention therapies (e.g., cardiac, autonomic, etc.), various exemplary mechanisms optionally aid in selecting and/or administering other therapies, such as, but not limited to, drug therapies and ablation therapies. For example, an exemplary method optionally includes administering one or more drugs at one or more concentrations with respect to time.

Various exemplary methods optionally include pacing at one or more rates to induce potential precursors to arrhythmia. For example, pacing at an elevated rate may induce alternans. Yet other pacing may treat a condition that has caused alternans.

Cardiac Rhythms

Figure 3:
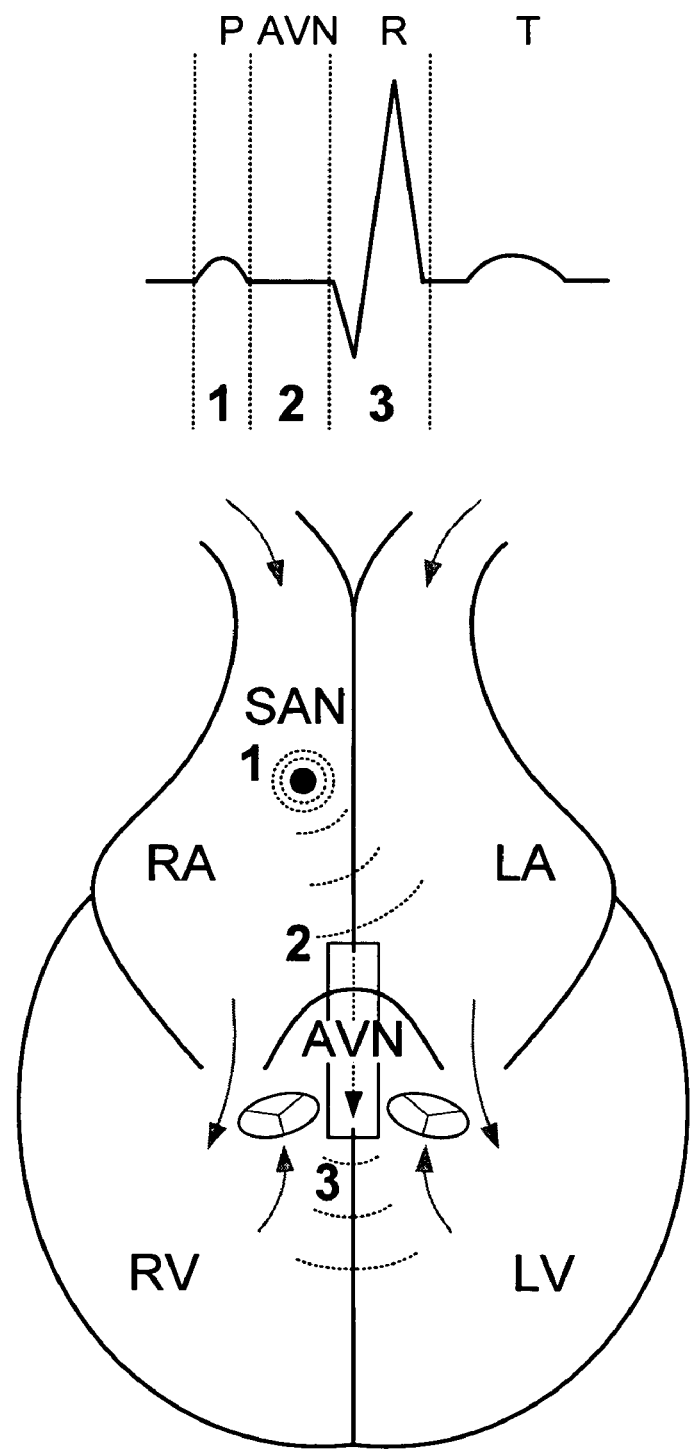
FIG. 3 is an approximate anatomical diagram of a heart and a waveform or ECG.

FIG. 3 shows an approximate anatomical diagram of a heart and an intrinsic waveform 300. Action potentials propagating through a normal heart are labeled as follows: 1, associated with the sinoatrial node (SAN) and the atria; 2, associated with the atrioventricular node and/or atrioventricular bundle (AVN); and 3, associated with the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes ventricular contraction. Thus, in a normal heart, ventricular rhythm relies on conduction of action potentials through the AV node and AV bundle (collectively referred to as the AV node or AVN).

An ECG of normal heart activity (e.g., polarization, depolarization, repolarization, etc.) typically shows atrial depolarization as a "P wave", ventricular depolarization as an "R wave", or QRS complex and ventricular repolarization as a T wave. The time span between a P wave and an R wave typically depends on AVN conduction and/or heart rate (e.g., rate of SAN). An ECG may also allow for determination of a QT interval, for example, measured from onset of a QRS complex to the end of ventricular repolarization (e.g., end of T wave). Yet further, an ECG may allow for determination of a ST interval, for example, measured from the end of a QRS complex to the end of a ventricular repolarization.

Figure 4:
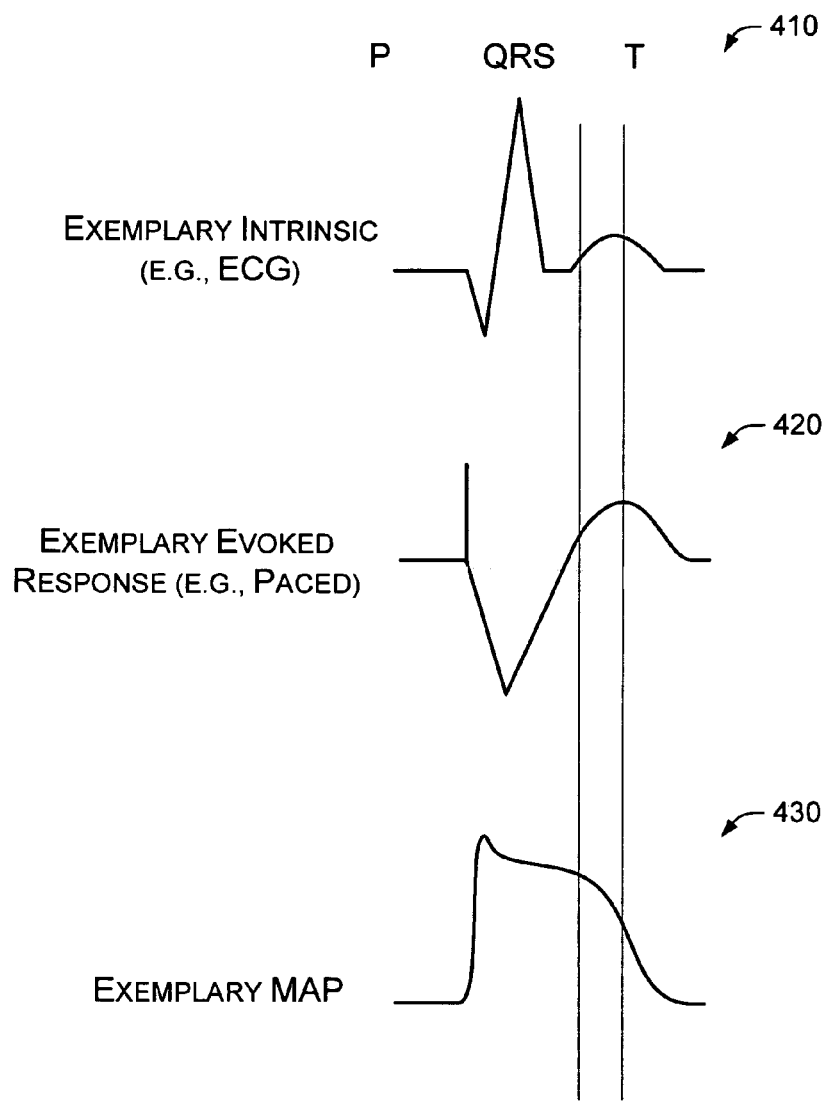
FIG. 4 is a diagram of various waveforms, including an intrinsic waveform, an evoked response and an action potential.

FIG. 4 shows part of an ECG 410 that includes a QRS complex and a T wave; an evoked response 420 that includes a stimulation artifact, a depolarization waveform and a repolarization waveform; and a monophasic action potential (MAP) that extends, approximately, over a QT interval. Various studies indicate that vulnerability to cardiac electrical instability is heightened during the initial phase of the T wave. Where T wave alternans and/or repolarization heterogeneity are present, MAPs typically exhibit evidence of such phenomena. Of course, an action potential may be sensed and/or otherwise analyzed over any of a variety of intervals (e.g., QT, ST, etc.).

FIG. 5 shows a plot 430 of two exemplary MAPs, labeled 434 and 438. The MAPs 434, 438 exhibit various features, such as, duration (e.g., $\Delta t$) and amplitude (e.g., $\Delta X$). Further, during the initial phase of the T wave, variations in potential versus time may occur from one MAP to another MAP. local cardiac activation FIG. 5 also shows an approximate first derivative of the MAP 434 with respect to time 440. The first derivative 440 exhibits various features, such as, local maxima 1 and 3 and local minima 2 and 4. The local maxima 1, 3 and local minima 2, 4 correspond to inflection points in the MAP 434 (e.g., potential versus time). The local maximum 1 corresponds approximately to the onset of depolarization; hence, with respect to duration (e.g., $\Delta t$), a first derivative of a MAP may be used to help determine a MAP duration. In this example, the local maximum 1 corresponds to a value in potential per second (e.g., X mV/s). Further, the local maximum 3 corresponds approximately to commencement of a T wave. Again, variation in cardiac activity at or near commencement of a T wave may help to determine risk or onset of arrhythmia.

FIG. 5 also shows an approximate second derivative of the MAP 434 with respect to time 450. The local maxima 1 and 3 and local minima 2 and 4 of the first derivative 440 appear as zero intercepts 1, 2, 3 and 4, respectively, in the second derivative with respect to time plot 450. The second derivative of the MAP 434, in potential with respect to time squared, has a zero intercept that corresponds approximately to onset of a T wave, which may help to determine risk or onset of arrhythmia. In addition, two positive peaks are labeled 0 and 5. The peak labeled 0 corresponds approximately to the beginning of the rise in the plot 430 while the peak labeled 5 corresponds approximately to the end of the T wave (e.g., represented by the peak having amplitude X mV per second squared). Thus, the peak labeled 5 can provide a rather accurate indication and/or time for the end of the repolarization.

Hence, as shown in FIG. 5, onset of a MAP may be ascertained or approximated using a first derivative of the MAP with respect to time and end of a MAP may be ascertained or approximated using a second derivative of the MAP with respect to time. Further, commencement of ventricular repolarization (e.g., a T wave), may be ascertained or approximated using a first derivative and/or a second derivative of the MAP with respect to time.

While FIG. 5 discusses MAPs with respect to time derivatives, information may be acquired with respect to position, for example, a direction in which the activation potential is traveling. The second derivative of a MAP with respect to position may yield information on volume source density as in theory the second derivative with respect to position of a MAP along an axon is proportional to volume source density. Such information may be provided from sensors at multiple sites and/or changes in sensing electrode configuration.

In general, whether an action potential (e.g., MAP, IEGM, etc.) or other signal, various exemplary mechanisms (e.g., methods, devices, systems, etc.) rely on information germane to repolarization. Such information may allow for determinations of duration, morphology, amplitude, etc., of a repolarization signal. In some instances, duration alone may fail to indicate abnormal or risky behavior. For example, some patients having genetic disposition for long QT syndrome have normal QT interval times. Thus, various exemplary mechanisms described herein may rely on any of a variety of measures related to repolarization, including temporal and/or spatial information.

Figure 6:
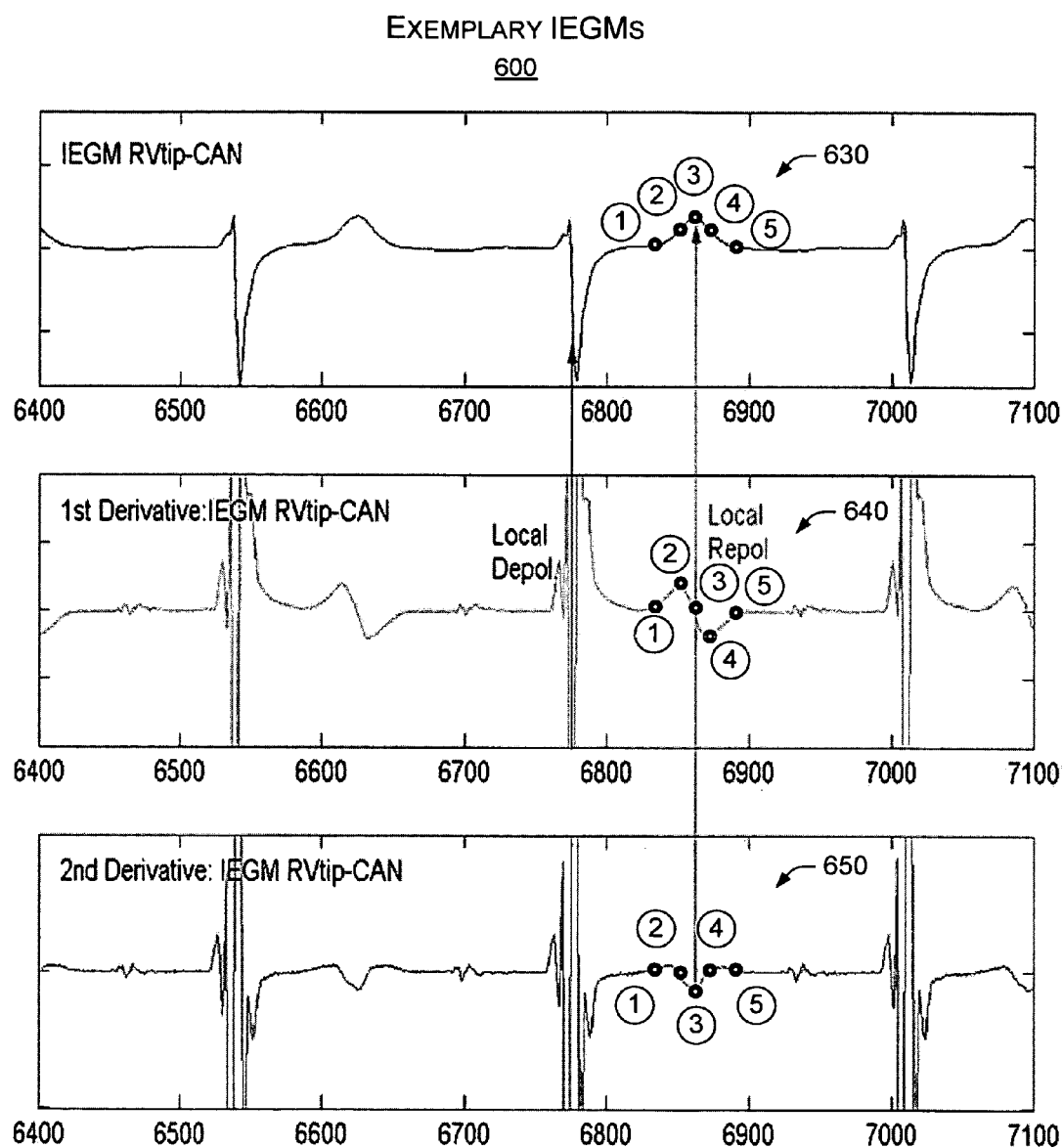
FIG. 6 is a diagram of various IEGMs and a first and a second derivative of a selected IEGM with respect to time.

FIG. 6 shows exemplary IEGMs 600 that include information related to repolarization. A first plot 630 of signal (e.g., potential in mV) versus time (e.g., in ms) includes several depolarization spikes and repolarization curves. One of the repolarization curves includes labels 1, 2, 3, 4 and 5 that represent various points of a repolarization curve. For example, point 1 corresponds to a rise in potential from a relatively flat baseline, point 2 corresponds to a relatively constant rise in potential versus time, point 3 corresponds to a peak in potential while point 4 corresponds to a relatively constant fall in potential versus time and point 5 corresponds to a return to a relatively flat baseline.

A second plot 640 is of the first derivative of potential with respect to time (e.g., in mV/s) versus time for the potential information of the first plot 630. In the plot 640, the point 2 now corresponds to a positive peak in the first derivative, point 3 corresponds approximately to a crossing of a baseline from a positive to a negative value, and point 4 corresponds to a negative peak in the first derivative. Thus, the first derivative of the potential may aid in detection of various information for purposes of alternans analysis, for example, as described further below.

A third plot 650 is of the second derivative of the potential with respect to time (e.g., in $mV/s^2$) versus time for the potential information of the first plot 630. In the plot 650, point 2 corresponds approximately to a crossing of a baseline from positive to negative, point 3 corresponds to a negative peak (e.g., a maximum) or maxima, and point 4 corresponds approximately to a crossing of a baseline from negative to positive. Thus, the second derivative of the potential may aid in detection of various information for purposes of alternans analysis, for example, as described further below. For example, various exemplary methods may use one or more time derivatives as information for alternans analysis. In some instances, a first and/or a second time derivative may allow for more accurate analysis than that provided by an unaltered IEGM. Of course, an analysis may rely on information in an unaltered signal and/or a derivative signal. Integrals and other techniques may optionally be used for an analysis.

For the information of the plots 630, 640 and 650, polarity of electrodes and associated sensing circuits may result in deviations from baseline that are different than those mentioned; however, regardless of electrode arrangement such information as exhibited by the labeled points is generally retained and available upon sensing.

While various points are illustrated in the plots of FIGS. 5 and 6, other points, segments defined by points, features of a signal, analysis techniques, etc., may be used. In general, an analysis aims to determine differences in a signal associated with one beat and a signal associated with another beat. Of course, an analysis may look at pairs of beats or other groupings. An analysis may examine signals on a temporal and/or spatial basis.

Figure 7:
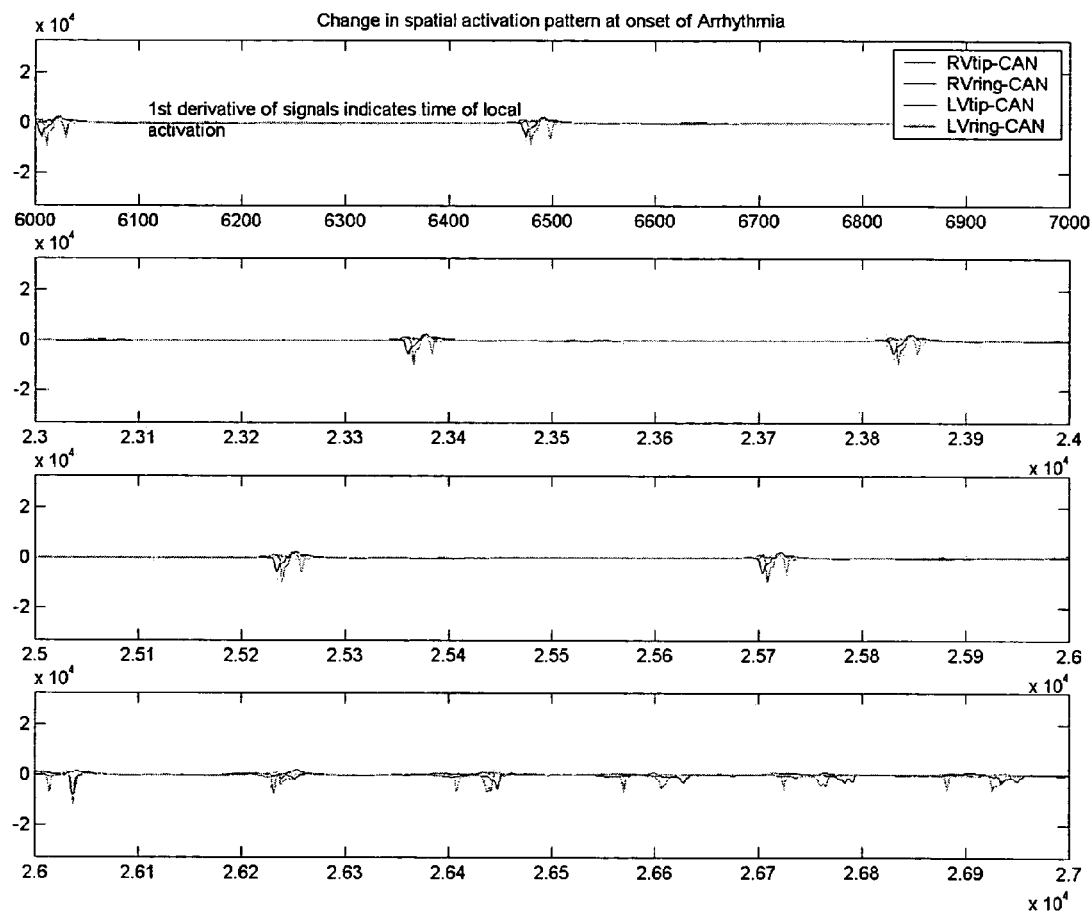
FIG. 7 is an IEGM that includes information acquired from a plurality of sensing sites and/or sensing configurations that show changes in spatial characteristics with respect to time.

The exemplary information presented in FIGS. 5 and 6 corresponds to temporal information at, for example, a single sensing site. As described herein, spatial information acquired at one or more sites and/or using one or more sensing configurations (e.g., electrode arrangements) may aid in arrhythmia detection, prevention and/or treatment therapy. FIG. 7 shows an exemplary progression 700 of spatial and temporal information as the first derivative of potential with respect to time versus time. In this example, four sensing configurations were used having the following electrode arrangements: RV-tip electrode to can electrode, RV-ring electrode to can electrode, LV-tip electrode to can electrode and LV-ring electrode to can electrode. Of course, bi-polar or other arrangements may provide similar spatial and/or temporal information.

At a time of approximately 6,500 ms, differences in spatial information exist and such differences become quite significant at a time of approximately 26,900 ms, which corresponds to an arrhythmia. Thus, the spatial information of the plot 700 indicates how spatial information may deviate during on-set and during an arrhythmia.

Thus far, various examples of temporal and spatial information have been presented and discussed with respect to various features that may allow for detection, prevention and/or treatment therapy for arrhythmias. Further discussion focuses on alternans and information germane to temporal and/or spatial differences in alternans.

Alternans Detection (T Wave and/or APs)

As already mentioned, T wave alternans or AP alternans have been shown to be associated with onset of arrhythmia. Alternans may be referred to as temporally and/or spatially concordant or discordant. In general, temporally and/or spatially concordant alternans are characterized by alternans (e.g., pairs of T waves or action potentials) that have some degree of regularity with respect to various features. In contrast, temporally and/or spatially discordant alternans have a lesser degree of regularity with respect to various features. A study by Qu, et al., "Mechanisms of Discordant Alternans and Induction of Reentry in Simulated Cardiac Tissue", *Circulation*, 102;1664–1670 (2000), reported that a transition from concordant to discordant action potential duration (APD) alternans is also a harbinger of vulnerability to ventricular arrhythmia (e.g., ventricular fibrillation). In particular, Qu, et al., reported that with an increasing pacing rate, "APD first alternates concordantly throughout tissue (causing T-wave alternans) and then becomes spatially discordant, with areas of long-short APD alternation adjacent to areas with short-long APD alternation (causing both QRS and T-wave alternans)". Qu, et al., noted that "this spatially out-of-phase APD alternation reflects a state of markedly increased dispersion of refractoriness, which predisposes the heart to wavebreak and initiation of reentry". Overall, Qu, et al., suggest that an increased dispersion of refractoriness arising from dynamic factors (e.g., APD and conduction velocity restitution properties) plays an important role in induction of ventricular reentry and that "reduction of dynamically induced dispersion by appropriate alteration of electrical restitution has promise as an antiarrhythmic strategy". More specifically, Qu, et al., reported that steeper APD restitution (e.g., APD plotted versus diastolic interval) was more likely to lead to discordant alternans when compared to shallow APD restitution. The reference by Qu, et al., is incorporated by reference herein.

Single site sensing may detect onset of temporally discordant alternans. However, as described herein, multisite sensing (e.g., including multi-electrode configuration sensing wherein one or more electrodes are optionally at a single site) may detect discordant alternans and spatial differences between cardiac alternans, i.e., temporally and/or spatially discordant alternans. For example, FIG. 8 shows exemplary APs 800 acquired from sensing at two different sites: Site 1 and Site 2. Sensing at the two different sites may include use of one or more common electrodes; however, polarity of such one or more common electrodes need not be the same for both sites. Sensing is optionally unipolar (e.g., a common case electrode), bipolar or a higher polarity (e.g., tripolar, etc.).

The Site 1 information shows four alternans (e.g., four pairs of APs). Each AP is labeled either "a" or "b". The various regularly alternating features of the APs labeled Ia/Ib, IIa/IIb, IIIa/IIIb and IVa/IVb would lead to a conclusion that such APs are fairly concordant. In contrast, the Site 2 information shows four altenans (e.g., four pairs of APs) that have fairly discordant alternating features. For example, at Site 2, the shape of the AP Ia varies to some degree with respect to the APs IIa, IIIa and IVa. Varying characteristics include duration, amplitude, activation time, repolarization end time. Yet further, characteristics of the APs Ib, IIb, IIIb and IVb vary to some degree as well, either in shape, etc., or in their relation to the APs Ia, IIa, IIIa and IVa.

A table of exemplary characteristics appears in FIG. 8 below the Site 1 and Site 2 AP plots. Of course, characteristics other than amplitude, duration, and T wave start time are optionally used to determine whether the APs at Site 1 and Site 2 are temporally concordant, temporally discordant and/or spatially different to some degree.

On the basis of such information, a risk or action hierarchy may be established. Actions may be optionally selected from a group of actions, which may or may not be in a hierarchy. Further, a condition may have a corresponding action, which may be optionally implemented by an implanted stimulation device (e.g., the device 100 of FIG. 1). Such a device may rely on a map, a look-up table, a model, etc., to determine an action for a corresponding condition.

Figure 9:
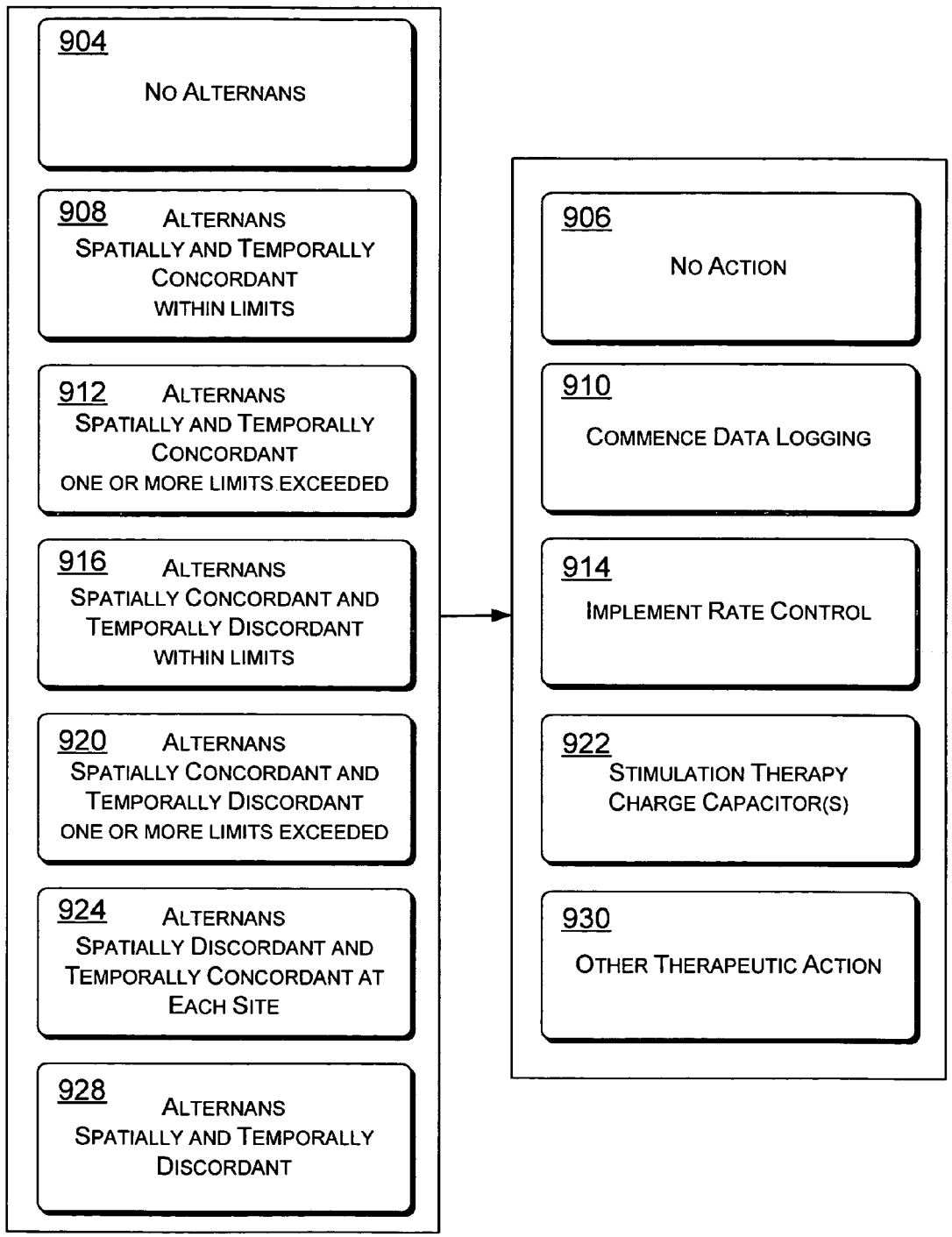
FIG. 9 is a block diagram of various conditions and optional actions that may occur in response to such conditions.

FIG. 9 shows an exemplary condition and an action hierarchy 900. A hierarchy may aid in determining therapy, control, device operation, etc. According to the hierarchy 900, at the lowest risk, is a no alternans block 904 which may have a corresponding no action block 906. A higher degree of patient risk exists for an alternans block 908 wherein the alternans are spatially and temporally concordant, for example, within one or more limits. The one or more limits may be based on information or parameters such as those discussed with reference to or presented in FIGS. 5, 6, 7, or 8. According to the hierarchy 900, a control command may follow per the commence data logging block 910. In this scenario, an implanted device may begin logging data related to alternans. Often data storage is limited, thus a feature that commences data logging upon occurrence of a certain alternans-based condition may benefit detection, prevention and/or treatment of arrhythmias and at the same time conserve resources when such a condition does not exist.

A spatial and temporal concordant alternans block 912 wherein one or more limits have been exceeded corresponds to a higher degree of patient risk. In this example, a control command may cause an implanted device to implement a therapy such as rate-based control per the implementation block 914. A spatially concordant and temporally discordant alternans block 916 wherein behavior does not exceed any particular alternans limit may corresponds to a higher degree of patient risk. Such an indication may call for rate-based control, for example, via the implementation block 914. A situation where one or more limits have been exceeded appears in the block 920. This situation may present a significant patient risk and call for action such as stimulation therapy and/or charging of one or more capacitors per the action block 922.

Another condition block 924 includes alternans that spatially discordant and temporally concordant at each site. A corresponding action block 922 may call for action such as stimulation therapy and/or charging of one or more capacitors. The stimulation therapy (e.g., cardiac, nerve, autonomic, etc.) aims to at least correct for the spatial discordance and/or to prevent worsening of the condition. A final block 928 in the hierarchy 900 indicates spatially and temporally discordant alternans. Such a condition is generally indicative of progression to or occurrence of an arrhythmia, accordingly the action block 930 may correspond to this condition and call for a therapeutic action that aims to quickly terminate the condition, for example, charging of one or more capacitors and delivery of a shock.

Various examples optionally use autonomic nerve stimulation or other mechanisms that aim to adjust or balance autonomic activity (e.g., parasympathetic and/or sympathetic activity); such therapeutic action may act to lesson conditions attributed to a high sympathetic tone and/or low parasympathetic tone. For example, if repolarization alternans occur in the presence of ischemia or high sympathetic drive, then vagal or parasympathetic stimulation may act to lessen the risk of occurrence and/or treat an occurrence. Such exemplary therapy may be responsive to the presence of alternans and/or temporal concordance, spatial concordance, temporal discordance, and/or spatial discordance of one or more characteristics in action potential signals (e.g., repolarization duration, amplitude, etc.).

Again, the various conditions presented in the blocks 904, 908, 912, 916, 920, 924 and/or 928 may be detected using information such as that discussed with reference to or presented in FIGS. 5, 6, 7 and 8. Further details of some information is shown in FIG. 10. In particular, FIG. 10 shows how such information 1000 may be used to determine alternan characteristics. For example, at Site 1, a difference in amplitude between AP Ia (e.g., A(Ia,1)) and AP Ib (e.g., A(Ib,1)) is represented as ΔA(I,1). A regular and repeating difference between alternating AP amplitudes (e.g., ΔA(I,1) to ΔA(II,1) to ΔA(III,1) to ΔA(IV,1), etc.) may indicate the presence of alternans. Further, if such a difference is regular, then the alternans may be characterized as temporally concordant; however, if such a difference is not regular, but still alternating to some degree, then the alternans may be characterized as temporally discordant. Similar types of analyses are optionally undertaken for duration (e.g., ΔΔt(I,1) to ΔΔt(II,1), etc.) and for T wave start (e.g., ΔTS(I,1) to ΔTS(II,1), etc.). Yet further, such analyses are optionally performed with respect to Site 2, for example, ΔA(I,2) to ΔA(II,2), etc.; ΔΔt(I,2) to ΔΔt(II,2), etc.; and ΔTS(I,2) to ΔTS(II,2), etc. Hence, the various exemplary analyses shown in FIG. 10 are optionally used to determine whether alternans exists at one or more sensing sites and, if alternans exist at one or more of the one or more sites, then such analyses are optionally used to determine whether the alternans are temporally and/or spatially concordant and/or discordant. For example, the analyses are optionally used to determine spatial differences in alternans at Site 1 and Site 2, wherein spatial differences can include temporal differences, i.e., differences with respect to time.

FIG. 11 shows various exemplary analyses 1100 for spatial differences in APs at a first site, Site 1, and a second site, Site 2. For example, such analyses include an amplitude difference (Adiff) for a first MAP at Site 1 (A(Ia,1)) and a corresponding first AP at Site 2 (A(Ia,2)), a duration difference (Δtdiff) for a first MAP at Site 1 (Δt(Ia,1)) and a corresponding first AP at Site 2 (Δt(Ia,2)), a time of activation difference (time activation-diff) for a first MAP at Site 1 and a corresponding first AP at Site 2, a end time of repolarization difference (time repolarization-diff) for a first AP at Site 1 and a corresponding first AP at Site 2, and a T wave start difference (TSdiff) for a first AP at Site 1 and a corresponding first AP at Site 2. Of course, similar differences exist for second APs, for example, a second AP in an alternans pair.

Yet other exemplary analyses include a difference of amplitude differences at a first site and a second site for corresponding alternans (ΔAdiff), a difference of AP duration differences at a first site and a second site for corresponding alternans (ΔΔtdiff), a difference of time of activation differences at a first site and a second site for corresponding alternans (Δtime activation-diff), a difference of an end of repolarization time differences at a first site and a second site for corresponding alternans (Δtime repolarization-diff), and a difference of T wave start time differences at a first site and a second site for corresponding alternans (ΔTSdiff).

FIG. 12 shows various exemplary analyses 1200 for three sensing sites. In this example, the differences between sites are optionally the absolute value of differences between sites (e.g., Site 1, Site 2 and Site 3). Of course, other data conditioning may take place to help arrive at a difference or other suitable measure. In this example, an activation time may be measured with respect to a prior activation time, with respect to an event, etc. For example, an activation time difference may result from sensing an event indicative of a first activation time (see, e.g., examples of FIG. 6) and sensing an event indicative of a second, later activation time wherein a timer commences upon the event of the first activation and terminates upon the event of the second activation. Of course, in this example, a timer may run continuously or discretely and mark a time for the first activation and a time for the second activation. In turn, a difference between these two times may be a time activation difference. Time differences for repolarization may occur in a similar manner, for example, based on one or more events noted in the plots of FIG. 6.

FIG. 13 shows various exemplary analyses 1300 for comparing various aforementioned differences to a baseline difference. For example, a baseline difference is optionally acquired during normal sinus rhythm and/or during pacing according to a prescribed pacing rate or rate function. Such information is then used to assess a "normal" state, for example, a state where no alternans exist, where concordant alternans exist that do not warrant intervention or increase risk of arrhythmia, where discordant alternans exist that do not warrant intervention or increase risk of arrhythmia, etc.

On an ongoing, periodic or other basis, an exemplary method implements sensing and analysis to generate a value that may be compared to a baseline value to determine whether a change in therapy is required, particularly, a change to reduce risk of arrhythmia, terminate arrhythmia, etc.

Figure 14:
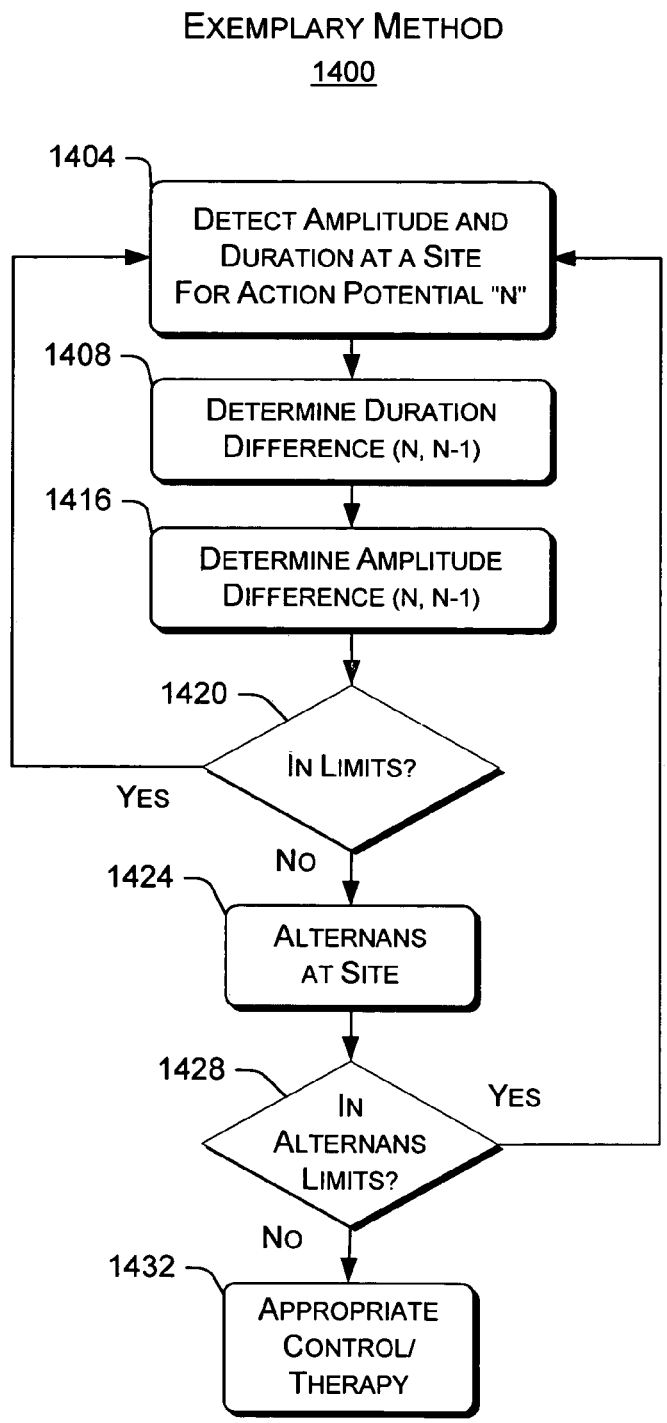
FIG. 14 is a block diagram of an exemplary method for alternans analysis at a single site.

FIG. 14 shows an exemplary method 1400 for alternans analysis at, for example, a single site. The exemplary method 1400 includes sensing or detecting various characteristics of an action potential or an IEGM (e.g., a MAP, T wave, etc.). In particular, the exemplary method 1400 includes a detection block 1404, wherein for an action potential "n", an amplitude and duration are detected at a site. A duration determination block 1408 follows that determines a duration difference for the action potential "n" and a prior action potential "n−1", which is typically the previous action potential (e.g., at a prior time). The exemplary method 1400 also includes an amplitude determination block 1416 that determines an amplitude difference for the action potential "n" and a prior action potential "n−1", which is typically the previous action potential.

According to the exemplary method 1400, a decision block 1420 follows that decides whether the duration difference of the determination block 1408 and/or the amplitude difference of the determination block 1416 are within limits. For example, a duration difference limit may exist for a duration difference whereby if a duration difference exceeds the limit, alternans exist (e.g., alternans block 1424) and an amplitude difference limit may exist for an amplitude difference whereby if an amplitude difference exceeds the limit, alternans exist (e.g., alternans block 1424). Of course, an "and/or" approach may be used in deciding whether alternans exist. Further, an alternative exemplary method may rely on only one measure, for example, a measure selected from the characteristics presented in FIG. 8 and/or FIG. 10. Yet further, an exemplary method may rely on more than two measures.

Referring again to FIG. 14, the exemplary method 1400 continues at the detect block 1404 if the decision block 1420 decides that the particular measures are within the limits. As mentioned, if the measures are not within the specified limits, the method 1400 continues in the alternans block 1424. Upon recognition of alternans, the method 1400 continues in another decision block 1428 that decides if the alternans are within one or more alternans limits. If the alternans are within the one or more limits, the method 1400 continues in the detection block 1404; however, if the decision block 1428 decides that the alternans are not within the one or more limits, then the method 1400 continues in a control/therapy block 1432. The control/therapy block 1432 institutes appropriate control or therapy suited to the alternans and the risk that the alternans may pose. For example, the alternans may indicate imminent onset of fibrillation and hence a fibrillation avoidance therapy may be implemented.

Figure 15:
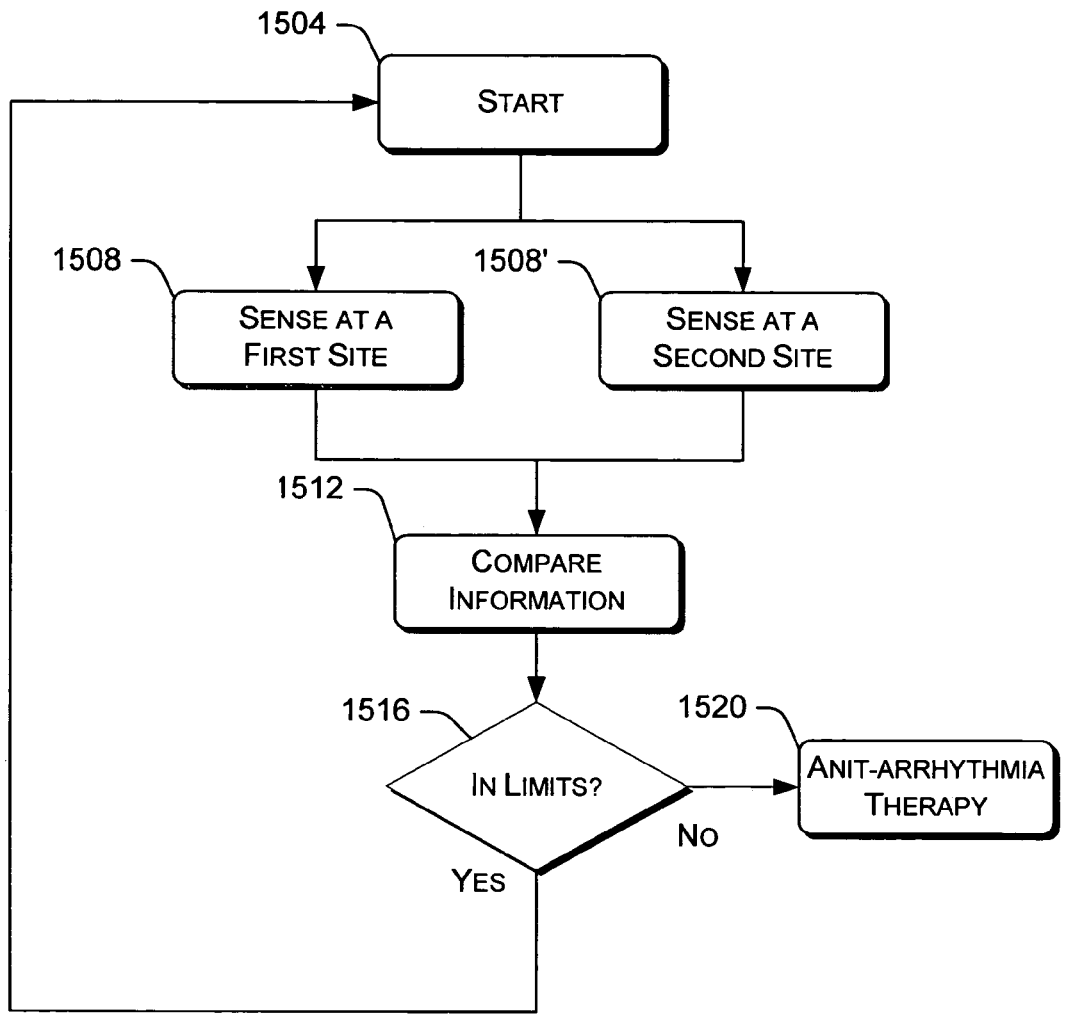
FIG. 15 is a block diagram of an exemplary method for sensing at a plurality of sites and for optionally administering anti-arrhythmia therapy.

FIG. 15 shows an exemplary method 1500 that includes sensing at a plurality of sites. The method 1500 commences at a start block 1504. The start block 1504 causes sensing to occur at a plurality of sites. A first sense block 1508 includes sensing at a first site and a second sense block 1508' includes sensing at a second site. A comparison block 1512 compares information acquired at the two sites, optionally with other information. A decision block 1516 may decide whether the comparison indicates behavior that falls outside of one or more limits. If the decision block 1516 decides that one or more limits have been exceeded or violated, then a therapy block 1520 may deliver suitable anti-arrhythmia therapy. If the decision block 1516 decides that no limits have been violated (e.g., that the behavior is acceptable), then the method 1500 may continue at the start block 1504.

The exemplary method 1500 optionally includes receiving an action potential signal associated with a myocardial contraction sensed at a myocardial site, receiving an action potential signal associated with the myocardial contraction sensed at a different myocardial site, comparing a common characteristic of each of the action potential signals wherein the common characteristic relates to at least one member selected from the group consisting of depolarization of tissue at the myocardial sites and repolarization of tissue at the myocardial sites, and, based on the comparing, deciding whether to call for anti-arrhythmia therapy.

While the exemplary method 1500 has been set forth in a fairly general manner, the various blocks may include more specific acts. For example, each sensing of the sense blocks 1508, 1508' may occur through use of one or more electrodes, for example, in a unipolar, bipolar or other manner. In general, a bipolar electrode configuration, that uses two electrodes having an interelectrode spacing of less than approximately 15 cm, can sense a more localized action potential when compared to a unipolar electrode configuration, which typically has a greater interelectrode spacing (e.g., tip, ring, etc. to case). Further, more closely spaced electrode typically result in a more localized signal. While spatial information may be obtained using one or more unipolar configurations, various exemplary methods use at least one bipolar or tripolar electrode configuration to obtain a more localized signal.

After sensing at the first site 1508 and at the second site 1508', a comparison block 1512 includes comparing one or more characteristics of sensed information at the first site and the second site. For example, a difference between amplitude, duration, activation time, end of repolarization time, T wave start time, etc. may be ascertained for information sensed at the first site and information sensed at the second site. Further, the comparison block optionally includes comparing to sensed information to one or more baseline values, which may be entered and/or previously sensed. A decision block 1516 follows that includes determining whether the comparison falls within or exceeds one or more limits, for example, one or more predetermined limits. The decision block 1516 may decide for example whether alternans exists, whether alternans are concordant at one or more sites, whether alternans are spatially discordant, whether alternans are temporally discordant, etc. Of course, the decision block 1516 may decide without making any specific determination as to whether alternans exist.

As appropriate, if one or more limits are not met, then the exemplary method 1500 continues in an anti-arrhythmia therapy block 1520. The anti-arrhythmia therapy block 1520 includes one or more therapies that are optionally selected based at least in part on the comparison and/or the one or more limits that have been exceeded. If the decision block 1516 decides that no limits have been exceeded, then the method 1500 continues, for example, at the start block 1504.

Figure 16:
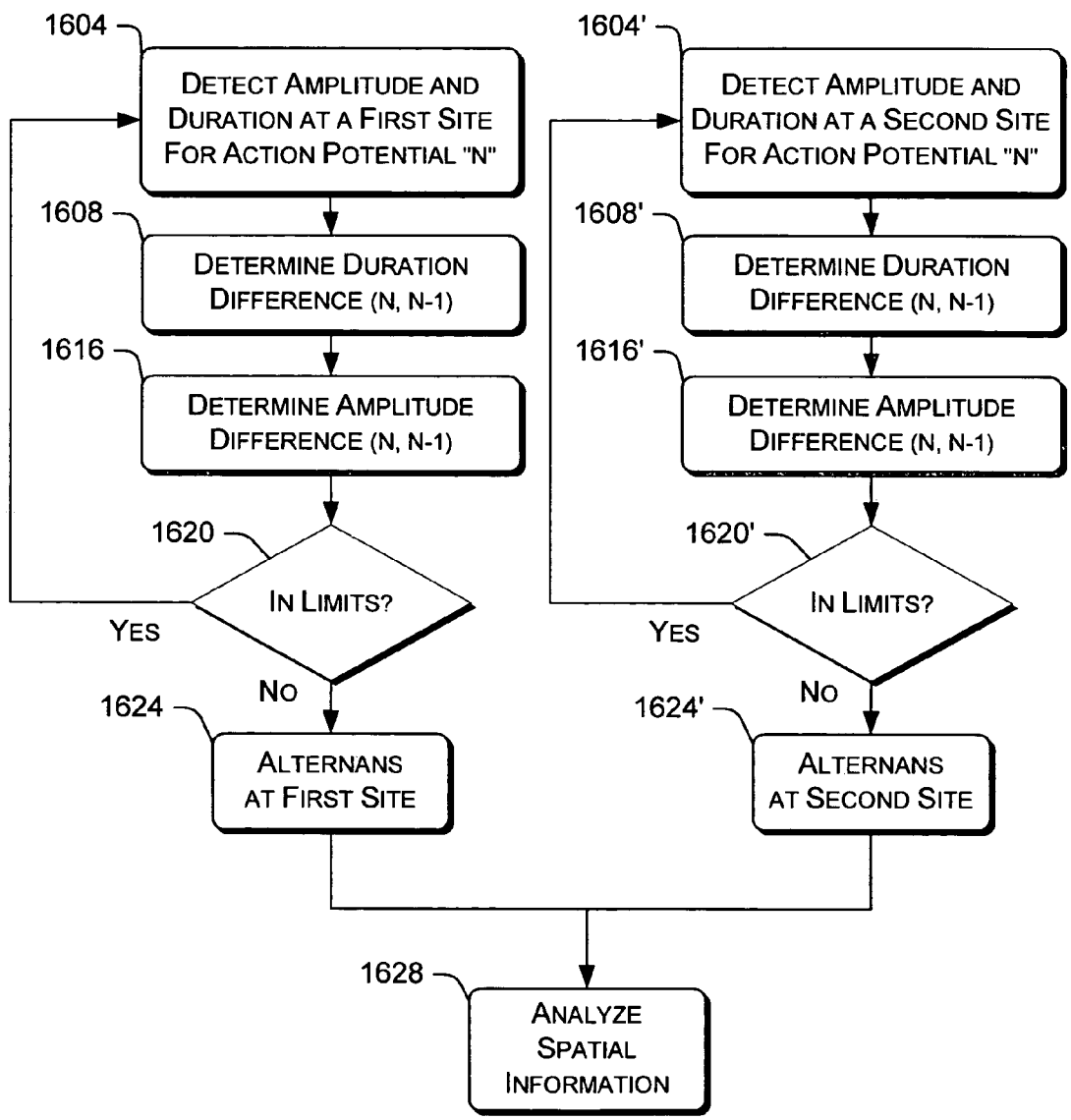
FIG. 16 is a block diagram of an exemplary method for detecting waveform characteristics at a plurality of sites and deciding whether alternans exist at any of the sites.

FIG. 16 shows another exemplary method 1600 that includes detecting various characteristics of an action potential (e.g., a MAP, T wave, etc.) at a plurality of sites prior to an analysis of spatial information. In a detection block 1604, for an action potential "n", an amplitude and duration are detected at a first site. In another detection block 1604', for the action potential "n", an amplitude and duration are detected at a second site. A duration determination block 1608 follows for the first site that determines a duration difference for the action potential "n" and a prior action potential "n−1", which is typically the previous action potential. Another duration determination block 1608' follows for the second site that determines a duration difference for the action potential "n" and a prior action potential "n−1". An amplitude determination block 1616 follows for the first site that determines an amplitude difference for the action potential "n" and a prior action potential "n−1", which is typically the previous action potential. Another amplitude determination block 1616' follows for the second site that determines an amplitude difference for the action potential "n" and a prior action potential "n−1".

In this example, for the first site and the second site, respective decision block 1620, 1620' follow the determination blocks 1608, 1608', 1616, 1616'. The decision block 1620 relies on one or more of the differences from the determination blocks 1608, 1616 to decide whether alternans exist at the first site; whereas, the decision block 1620' relies on one or more of the differences from the determination blocks 1608', 1616' to decide whether alternans exist at the second site. While the exemplary method 1600 relies on amplitude and duration, such a method may optionally use other additional or alternative characteristics of an action potential to decide whether alternans exist at the first site, the second site and/or another site. If alternans exist at the first site, then the method 1600 continues at the alert block 1624 and if alternans exist at the second site, then the method 1600 continues at the alert block 1624', acknowledging that the method 1600 optionally continues at neither of the alert blocks 1624, 1624', at one of the alert blocks 1624, 1624', or at both alert blocks 1624, 1624'. Entering an alert block may prevent a branch of the method 1600 from continuing back to its respective detection block. For example, according to the exemplary method 1600, if the decision blocks 1620, 1620' decide that alternans are not present (e.g., no limits exceeded, etc.), then the method 1600 continues at the respective detection blocks 1604, 1604'. According to the exemplary method 1600, the alert blocks 1624, 1624' continue to an analysis block 1628 wherein spatial analysis of detected information may occur. The spatial analysis may determine whether the alternans at the first site and at the second site are temporally and/or spatially concordant and/or discordant. For example, alternans at two sites may exhibit temporal discordance and spatial concordance.

Figure 17:
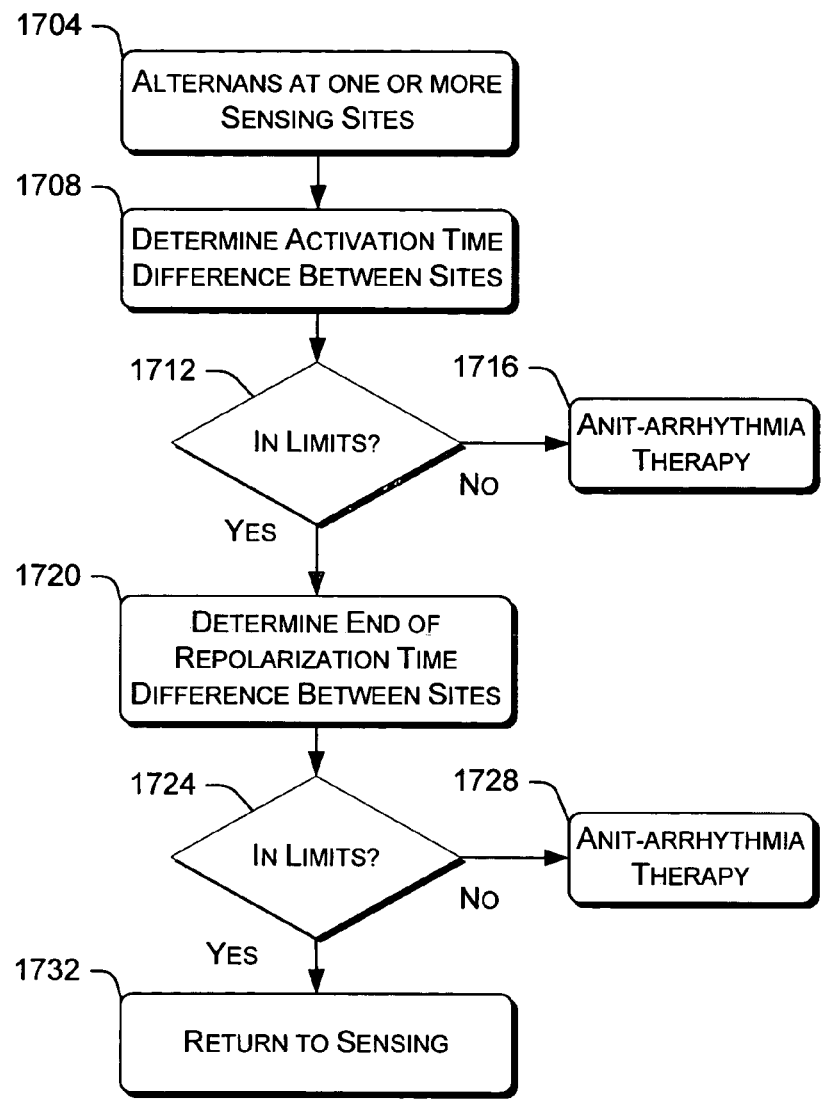
FIG. 17 is a block diagram of an exemplary method for analyzing activation times and end of repolarization times.

FIG. 17 shows an exemplary method 1700 that optionally follows from the exemplary method 1600 where the method 1600 enters the analysis block 1628. The method 1700 commences in a block 1704 that acknowledges the existence of alternans at one or more sensing sites. A determination block 1708 follows that determines an activation time difference for an action potential (e.g., action potential "n") sensed at the sites. Where two sensing sites are used, then only one activation time difference results (e.g., the difference between the activation time of the first site and the activation time of the second site). If three sensing sites are used, then more than one activation time difference exists. Of course, the types or numbers of differences may depend on which sites exhibit alternans.

A decision block 1712 follows wherein one or more differences in activation times (e.g., spatial differences) are compared to one or more limits. Of course, a sum of the differences or another function (e.g., weighted function, etc.) of activation times at different spatial positions may be compared to one or more limits. If at least one of the one or more differences does not compare favorably, then the exemplary method 1700 continues at an anti-arrhythmia therapy block 1716. However, if the decision block 1712 decides that no significant deviation occurred with respect to one or more limits, then the method 1700 continues in another determination block 1720. Of course, the determination block 1720 optionally occurs prior to or in conjunction with the determination block 1708. Further, decisions are optionally based at least in part on one or both of a spatial activation time difference or a spatial end of repolarization time difference.

While the exemplary method 1700 refers to activation time in block 1708, a beginning of repolarization time may be used as an alternative or in addition to the activation time. Various examples optionally rely on one or more characteristics of a repolarization signal to determine if a condition exists. Referring again to FIG. 6, an IEGM can provide repolarization information such as a beginning of repolarization time (e.g., point 1), maximum repolarization amplitude (e.g., point 3), a maximum repolarization amplitude time (e.g., point 3), an end of repolarization time (e.g., point 5). Other intermediate points of a repolarization signal may be optionally used to determine if a condition exists (e.g., spatial and/or temporal concordance, spatial and/or temporal discordance, alternans, etc.). One or more derivatives with respect to time may be used to identify or quantify such values. Integrals or other analysis techniques may be optionally used as alternatives or in addition to derivatives.

Referring again to FIG. 17, in this example, the determination block 1720 follows the decision block 1712 wherein the determination block 1720 determines an end of repolarization time difference for an action potential (e.g., action potential "n") sensed at the sites. Where two sensing sites are used, then only one end of repolarization time difference results (e.g., the difference between the end of repolarization time of the first site and the end of repolarization time of the second site). If three sensing sites are used, then more than one time difference exists. Of course, the types or numbers of differences may depend on which sites exhibit alternans. In an alternative, information may not exhibit alternans, but still exhibit informational differences that deviate with respect to one or more limits, etc. Such deviations may be significant and indicate a need for appropriate therapy.

A decision block 1724 follows the determination block 1720 wherein one or more differences in end of repolarization times (e.g., spatial differences) are compared to one or more limits. Of course, a sum of the differences or another function (e.g., weighted function, etc.) of repolarization times at different spatial positions may be compared to one or more limits. If at least one of the one or more differences does not compare favorably, then the exemplary method 1700 continues at an anti-arrhythmia therapy block 1728. However, if the decision block 1724 decides that no significant deviation occurred with respect to one or more limits, then the method 1700 continues in a return to sensing block 1732.

Figure 18:
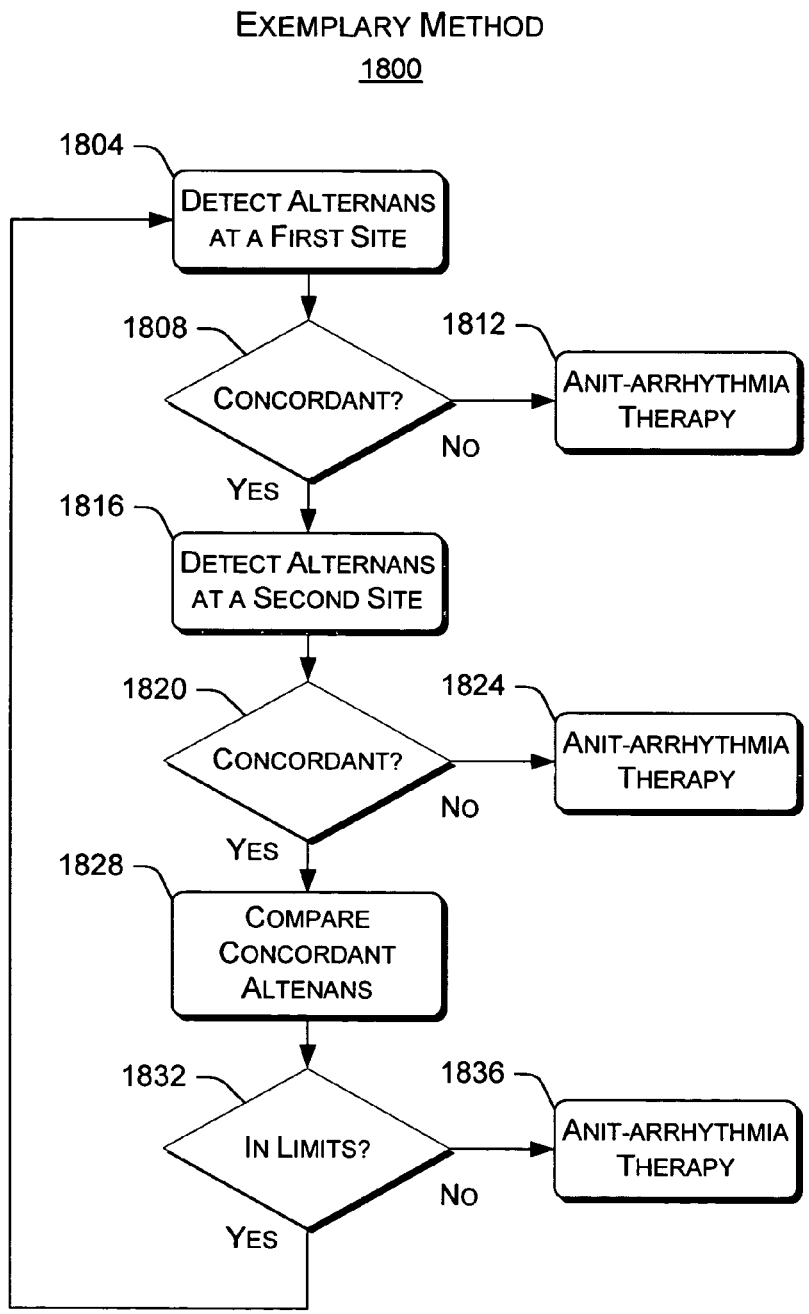
FIG. 18 is a block diagram of an exemplary method for deciding whether concordant alternans exists at one or more sites.

FIG. 18 shows another exemplary method 1800 that includes detecting alternans at one or more sensing sites. In a first detection block 1804, alternans are detected at a first sensing site. For example, alternans are optionally detected at least in part on the basis of one or more characteristics of an action potential, a T wave, etc. A decision block 1808 follows that decides whether the alternans at the first site are temporally concordant (or alternatively temporally discordant, etc.). If the decision block 1808 decides that the alternans at the first site are temporally concordant, then the method 1800 continues in another detection block 1816; however, if the decision block 1808 decides that the alternans are not concordant (e.g., temporally discordant, etc.), then the method 1800 continues in an anti-arrhythmia therapy block 1812.

The detection block 1816 detects alternans at a second sensing site. After such detection, the method 1800 continues in another decision block 1820 that decides whether the alternans at the second site are concordant (or alternatively discordant, etc.). If the decision block 1820 decides that the alternans at the second site are concordant, then the method 1800 continues in a comparison block 1828, which performs a spatial comparison or analysis of the alternans at the first site and the alternans at the second site. In general, a spatial comparison or analysis refers to a comparison or analysis of information from more than one site and, in particular, to determine if the difference between cardiac activity at the sites indicates that risk of arrhythmia has increased and/or that an onset of arrhythmia is imminent. A decision block 1832 follows that decides if the comparison or analysis violates any particular limit or limits. If the decision block 1832 decides that some spatial "discord" exists between the temporally concordant alternans at the first site and the temporally concordant alternans at the second site (e.g., spatial discord), then the method 1800 continues in an anti-arrhythmia therapy block 1836. Otherwise, the method 1800 continues at the detection block 1804 or at another appropriate point.

Figure 19:
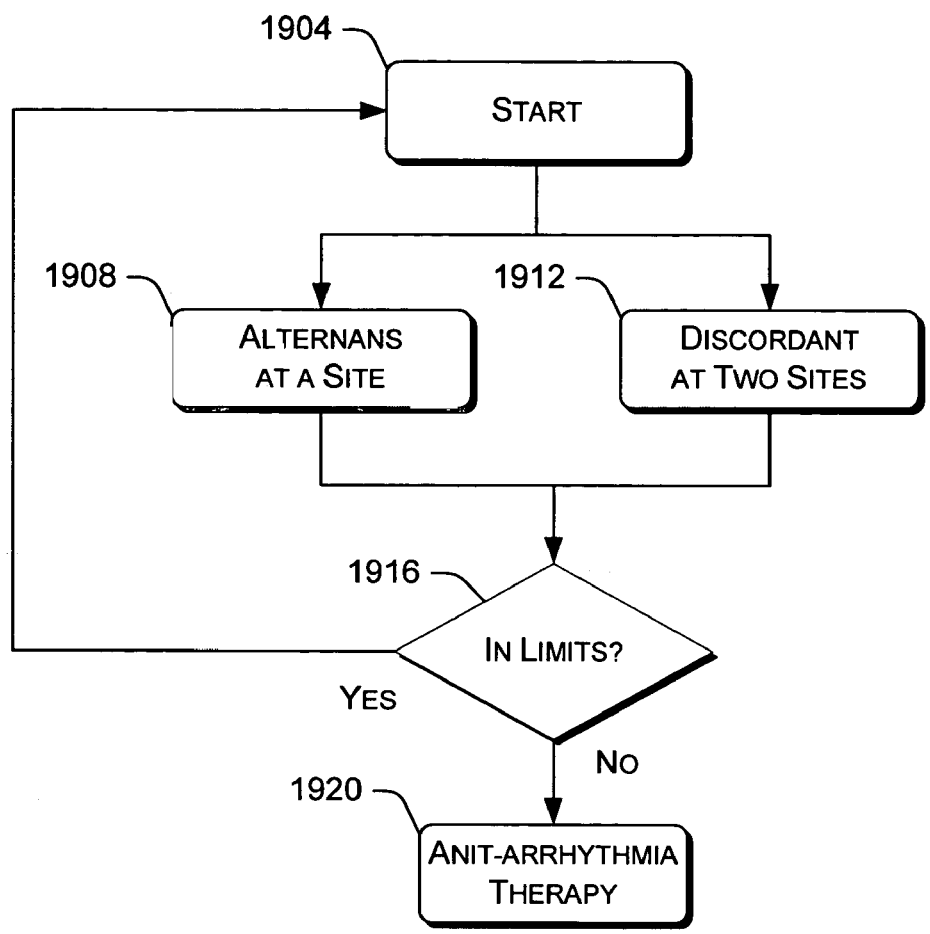
FIG. 19 is a block diagram of an exemplary method for administering anti-arrhythmia therapy in response to alternans at one or more site and/or in response to spatially discordant alternans (e.g., discordant between two or more sites).

FIG. 19 shows an exemplary method 1900 that includes alternans detection and spatially discordant information. The method 1900 commences at a start block 1904. The start block 1904, for example, causes sensing to occur at a plurality of sites and/or analysis of such sensing. An alternans block 1908 determines that alternans exist for at least one sensing site. A discordant information block 1912 determines that spatially discordant information exists between two or more sensing sites. In the exemplary method 1900, either event causes continuation at the decision block 1916. Of course, the method 1900 may optionally use some preliminary logic to determine whether to proceed to the decision block 1916. For example, if discordant per block 1912, then always proceed to the decision block 1916 while if alternans at a site, do not proceed to the decision block 1916 unless discordant information detected within the last x minutes (where x may be a few minutes to several days). In this manner, such a method may weigh when to use alternans at a site, or may weigh alternans at different sites differently. Table 1 shows sites associated with exemplary time periods for discordant information.

TABLE 1

Site related time since last discordant information.

| Site | Time |
|---|---|
| Right atrium | 8 hours |
| Right apex | 2 hours |
| Coronary sinus | 1 hour |
| Left ventricle | 0 hours |

In the example of Table 1, the closer the sensing site is to the left ventricle, the less the time period. If alternans exist at more than one site, then the shortest time period may dominant, or even a shortened period thereof. Of course, other possibilities exist.

The decision block 1916 optionally relies on the number of times alternans exist at the site or sites. For example, if the last five ventricular contractions resulted in alternans at a site, then this condition may be sufficient to call for the method 1900 to continue at the anti-arrhythmia therapy block 1920. As described elsewhere herein, the decision block 1916 optionally relies on characteristics of one or more action potentials. In general, discordant spatial information may be a better indicator of an increased risk of ventricular arrhythmia when compared to alternans information from a single site.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claims methods, devices, systems, etc.

The invention claimed is:

1. A method comprising:
receiving first, second, third and fourth action potential signals sensed at a first myocardial site, each of the first, second, third and fourth action potential signal associated with a respective first, second, third and fourth myocardial contraction;
comparing a common characteristic of the first and second action potential signals wherein the common characteristic relates to repolarization of tissue at the myocardial site to determine if alternans exists at the first myocardial site;
if alternans exists at the first myocardial site, comparing a common characteristic of the first, second, third and fourth action potential signals, wherein the common characteristic relates to repolarization of tissue at the myocardial site, to determine if the alternans at the first myocardial site is temporally concordant or temporally discordant; and
based on whether the alternans at the first myocardial site is concordant or discordant, initiating one or more type of anti-arrhythmia therapy.

2. The method of claim 1, wherein the common characteristic comprises duration of repolarization.

3. The method of claim 1, wherein the second myocardial contraction comprises the myocardial contraction subsequent the first myocardial contraction.

4. The method of claim 1, wherein a variation in the common characteristic indicates the presence of alternans.

5. The method of claim 1, further comprising:
receiving a fifth action potential signal associated with the first myocardial contraction sensed at a second myocardial site;
receiving a sixth action potential signal associated with the second myocardial contraction sensed at the second myocardial site;
comparing a common characteristic of the fifth and sixth action potential signals wherein the common characteristic relates to repolarization of tissue at the second myocardial site, to determine if alternans exists at the second myocardial site; and
if alternans exists at the first myocardial site and the second myocardial site, comparing the common characteristic of the first, second, fifth and sixth action potential signals to determine if the alternans between the first and second myocardial sites is spatially concordant or spatially discordant.

6. The method of claim 5, further comprising:
receiving a seventh action potential signal associated with the third myocardial contraction sensed at the second myocardial site;

receiving an eighth action potential signal associated with the fourth myocardial contraction sensed at the second myocardial site;

if alternans exists at the second myocardial site, comparing the common characteristic of the fifth, sixth, seventh and eighth action potential signals to determine if the alternans at the second myocardial site is temporally concordant or temporally discordant.

7. The method of claim 1 further comprising taking a derivative with respect to time for each of the action potential signals to determine a value of the common characteristic for each signal.

8. The method of claim 1 wherein comparing comprises comparing two common characteristics of the action potential signals and further comprising taking a first derivative with respect to time for each of the action potential signals to determine a value of a first common characteristic for each signal and taking a second derivative with respect to time for each of the action potential signals to determine a value of a second common characteristic for each signal.

9. The method of claim 1 wherein the signals comprise intracardiac electrogram signals.

10. One or more computer-readable media comprising instructions thereon which, when executed by a microprocessor, cause an implantable device:
to receive first, second, third and fourth action potential signals sensed at a first myocardial site, each of the first, second, third and fourth action potential signal associated with a respective first, second, third and fourth myocardial contraction;
to compare a common characteristic of the first and second action potential signals, wherein the common characteristic relates to repolarization of tissue at the myocardial site, to determine if alternans exists at the first myocardial site;
if alternans exists at the first myocardial site, to compare a common characteristic of the first, second, third and fourth action potential signals, wherein the common characteristic relates to repolarization of tissue at the myocardial site, to determine if the alternans at the first myocardial site is temporally concordant or temporally discordant; and
based on whether the alternans at the first myocardial site is concordant or discordant, to initiate one or more type of anti-arrhythmia therapy.

11. An implantable device comprising:
a microprocessor;
one or more inputs for receiving signals;
one or more outputs for delivering stimulation to tissue; and
memory including instructions thereon which, when executed by the microprocessor, cause the implantable device:
to receive first, second, third and fourth action potential signals sensed at a first myocardial site, each of the first, second, third and fourth action potential signal associated with a respective first, second, third and fourth myocardial contraction;
to compare a common characteristic of the first and second action potential signals wherein the common characteristic relates to repolarization of tissue at the myocardial site to determine if alternans exists at the first myocardial site;
if alternans exists at the first myocardial site, to compare a common characteristic of the first, second, third and fourth action potential signals, wherein the common characteristic relates to repolarization of tissue at the myocardial site, to determine if the alternans at the first myocardial site is temporally concordant or temporally discordant; and, based on whether the alternans at the first myocardial site is concordant or discordant, to initiate one or more type of anti-arrhythmia therapy.

12. A method comprising:
receiving first, second, third and fourth action potential signals sensed at a first myocardial site, each of the first, second, third and fourth action potential signal associated with a respective first, second, third and fourth myocardial contraction;
receiving fifth, sixth, seventh and eighth action potential signals sensed at a second myocardial site, each of the fifth, sixth, seventh and eighth action potential signals associated with the respective first, second, third and fourth myocardial contraction;
comparing a common characteristic of the first, second, third and fourth action potential signals wherein the common characteristic relates to at least one member selected from the group consisting of depolarization of tissue at the myocardial site and repolarization of tissue at the myocardial site to determine if temporal concordant or discordant alternans exists at the first myocardial site;
comparing a common characteristic of the fifth, sixth, seventh and eighth action potential signals wherein the common characteristic relates to at least one member selected from the group consisting of depolarization of tissue at the myocardial site and repolarization of tissue at the myocardial site to determine if temporal concordant or discordant alternans exists at the second myocardial site;
if temporal discordant alternans exists at one of the first myocardial site or the second myocardial site, initiating anti-arrhythmia therapy;
if temporal concordant alternans exist at both the first myocardial site and the second myocardial site, comparing a common characteristic of the first, second, third, fourth, fifth, sixth, seventh and eight action potential signals, wherein the common characteristic relates to at least one member selected from the group consisting of depolarization of tissue at the myocardial sites and repolarization of tissue at the myocardial sites, to determine if the alternans between the first and second myocardial sites is spatially concordant or spatially discordant; and
if the alternans between the first and second myocardial sites is spatially discordant, initiating anti-arrhythmia therapy.

13. The method of claim 12 wherein the signals comprise intracardiac electrogram signals.

14. The method of claim 12 wherein the common characteristic comprises an end of repolarization time.

15. The method of claim 12 wherein the common characteristic comprises a beginning of repolarization time.

16. The method of claim 12 wherein the common characteristic comprises duration of repolarization.

17. The method of claim 12 wherein the common characteristic comprises amplitude of repolarization.

18. The method of claim 12 wherein the common characteristic comprises maximum amplitude of repolarization.

19. The method of claim 12 wherein the common characteristic comprises a time for maximum amplitude of repolarization.

20. The method of claim 12 wherein comparing a common characteristic comprises comparing two or more common characteristics.

21. The method of claim 20 wherein at least one common characteristic relates to depolarization and at least one common characteristic relates to repolarization.

22. The method of claim 12 wherein the anti-arrhythmia therapy comprises autonomic nerve stimulation.

23. The method of claim 22 wherein the autonomic nerve stimulation increases parasympathetic tone.

24. One or more computer-readable media comprising instructions thereon, which when executed by a microprocessor, cause an implantable device:

to receive first, second, third and fourth action potential signals sensed at a first myocardial site, each of the first, second, third and fourth action potential signal associated with a respective first, second, third and fourth myocardial contraction;

to receive fifth, sixth, seventh and eighth action potential signals sensed at a second myocardial site, each of the fifth, sixth, seventh and eighth action potential signals associated with the respective first, second, third and fourth myocardial contraction;

to compare a common characteristic of the first, second, third and fourth action potential signals wherein the common characteristic relates to at least one member selected from the group consisting of depolarization of tissue at the myocardial site and repolarization of tissue at the myocardial site to determine if temporal concordant or discordant alternans exists at the first myocardial site;

to compare a common characteristic of the fifth, sixth, seventh and eighth action potential signals wherein the common characteristic relates to at least one member selected from the group consisting of depolarization of tissue at the myocardial site and repolarization of tissue at the myocardial site to determine if temporal concordant or discordant alternans exists at the second myocardial site;

to initiate anti-arrhythmia therapy if temporal discordant alternans exists at one of the first myocardial site or the second myocardial site;

if temporal concordant alternans exist at both the first myocardial site and the second myocardial site, to compare a common characteristic of the first, second, third, fourth, fifth, sixth, seventh and eight action potential signals, wherein the common characteristic relates to at least one member selected from the group consisting of depolarization of tissue at the myocardial sites and repolarization of tissue at the myocardial sites, to determine if the alternans between the first and second myocardial sites is spatially concordant or spatially discordant; and to initiate anti-arrhythmia therapy if the alternans between the first and second myocardial sites is spatially discordant.

25. An implantable device comprising:
a microprocessor;
one or more inputs for receiving signals;
one or more outputs for delivering stimulation to tissue; and
memory including instructions thereon which, when executed by the microprocessor, cause the implantable device:
to receive first, second, third and fourth action potential signals sensed at a first myocardial site, each of the first, second, third and fourth action potential signal associated with a respective first, second, third and fourth myocardial contraction;

to receive fifth, sixth, seventh and eighth action potential signals sensed at a second myocardial site, each of the fifth, sixth, seventh and eighth action potential signals associated with the respective first, second, third and fourth myocardial contraction;

to compare a common characteristic of the first, second, third and fourth action potential signals wherein the common characteristic relates to at least one member selected from the group consisting of depolarization of tissue at the myocardial site and repolarization of tissue at the myocardial site to determine if temporal concordant or discordant alternans exists at the first myocardial site;

to compare a common characteristic of the fifth, sixth, seventh and eighth action potential signals wherein the common characteristic relates to at least one member selected from the group consisting of depolarization of tissue at the myocardial site and repolarization of tissue at the myocardial site to determine if temporal concordant or discordant alternans exists at the second myocardial site;

to initiate anti-arrhythmia therapy if temporal discordant alternans exists at one of the first myocardial site or the second myocardial site;

if temporal concordant alternans exist at both the first myocardial site and the second myocardial site, to compare a common characteristic of the first, second, third, fourth, fifth, sixth, seventh and eight action potential signals, wherein the common characteristic relates to at least one member selected from the group consisting of depolarization of tissue at the myocardial sites and repolarization of tissue at the myocardial sites, to determine if the alternans between the first and second myocardial sites is spatially concordant or spatially discordant; and to initiate anti-arrhythmia therapy if the alternans between the first and second myocardial sites is spatially discordant.

26. An implantable device comprising:
means for receiving first, second, third and fourth action potential signals sensed at a first myocardial site, each of the first, second, third and fourth action potential signal associated with a respective first, second, third and fourth myocardial contraction;

means for receiving fifth, sixth, seventh and eighth action potential signals sensed at a second myocardial site, each of the fifth, sixth, seventh and eighth action potential signals associated with the respective first, second, third and fourth myocardial contraction;

means for comparing a common characteristic of the first, second, third and fourth action potential signals wherein the common characteristic relates to at least one member selected from the group consisting of depolarization of tissue at the myocardial site and repolarization of tissue at the myocardial site to determine if temporal concordant or discordant alternans exists at the first myocardial site;

means for comparing a common characteristic of the fifth, sixth, seventh and eighth action potential signals wherein the common characteristic relates to at least one member selected from the group consisting of depolarization of tissue at the myocardial site and repolarization of tissue at the myocardial site to determine if temporal concordant or discordant alternans exists at the second myocardial site;

means for initiating anti-arrhythmia therapy if temporal discordant alternans exists at one of the first myocardial site or the second myocardial site;

means for, if temporal concordant alternans exist at both the first myocardial site and the second myocardial site, comparing a common characteristic of the first, second, third, fourth, fifth, sixth, seventh and eight action potential signals, wherein the common characteristic relates to at least one member selected from the group consisting of depolarization of tissue at the myocardial sites and repolarization of tissue at the myocardial sites, to determine if the alternans between the first and second myocardial sites is spatially concordant or spatially discordant; and means for initiating anti-arrhythmia therapy if the alternans between the first and second myocardial sites is spatially discordant.

* * * * *